US006087358A

United States Patent [19]

Baker et al.

[11] Patent Number: 6,087,358

[45] **Date of Patent: *Jul. 11, 2000**

[54] NITRO-[2,1-B]IMIDAZOPYRAN COMPOUNDS AND ANTIBACTERIAL USES THEREOF

[75] Inventors: William R. Baker, Bellevue; Cai Shaopei; Eric L. Keeler, both of Seattle, all of Wash.

[73] Assignee: PathoGenesis Corporation, Seattle, Wash.

[ * ] Notice: This patent is subject to a terminal disclaimer.

[21] Appl. No.: 08/924,559

[22] Filed: Sep. 5, 1997

Related U.S. Application Data

[63] Continuation-in-part of application No. PCT/US96/10904, Jun. 25, 1996, which is a continuation-in-part of application No. 08/496,850, Jun. 26, 1995, Pat. No. 5,668,127.

[51] Int. Cl.[7] ........................ A61K 31/535; C07D 498/00

[52] U.S. Cl. ........................ 514/230.5; 544/91

[58] Field of Search ........................ 544/91; 514/230.5

[56] References Cited

U.S. PATENT DOCUMENTS 5,668,127 9/1997 Baker et al. ........................ 514/183

*Primary Examiner*—Mukund J. Shah
*Assistant Examiner*—Tamthom N. Truong
*Attorney, Agent, or Firm*—Christensen O'Connor Johnson & Kindness PLLC

[57] ABSTRACT

Methods, compounds and compositions are provided for inhibiting the growth of pathogenic microbes in vitro and of treatment of pathogenic bacterial infections, such as mycobacterial, Clostridium, Cryptosporidium and Helicobacter infections, in vivo using bicyclic nitroimidazole compounds of the formula (II):

(II)

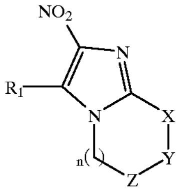

wherein $R_1$ is hydrogen, halogen, loweralkyl, haloloweralkyl, cycloalkyl, heterocycle, substituted heterocycle and heterocyclicalkyl; X is oxygen, sulfur or $NR_2$, where $R_2$ is hydrogen, loweralkyl, aryl, cycloalkyl, heterocycle, substituted heterocycle, heterocyclicalkyl, $COR_3$ or $SO_2R_4CONR_4R_5$, where $R_3$, $R_4$ and $R_5$ are independently selected from hydrogen, loweralkyl, aryl, alkylaryl, alkoxyalkyl, alkoxyaryl, alloxyalkoxyaryl, alkylheterocycle, and alkoxyheterocycle; n is 1, 2 or 3; Y and Z are independently selected from oxygen, $CH_2$, CO, $CR_4R_5$ or $NR_4$, where $R_4$ and $R_5$ are as defined above; provided that when n is 2 or 3, the compounds of formula II can be additionally substituted as follows:

(IIa)

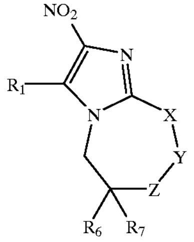

(IIb)

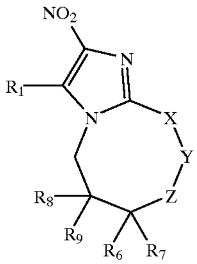

wherein $R_6$, $R_7$, $R_8$ and $R_9$ are independently selected from hydrogen, loweralkyl, aryl, alkylaryl, alkoxyalkyl, alkoxyalkylaryl, alkoxyalkylheterocycle, alkylary2alkylaryl, alkylarylaryl, alkylcycloalkyl, alkoxyaryl, alkylheterocycle, and alkoxyheterocycle; and the pharmaceutically acceptable salts thereof.

7 Claims, 5 Drawing Sheets

1
1a R = Cl
1b R = $NO_2$ 3
3a R = Cl
Z = $CR_2OH$
3b R = $NO_2$
Z = $CR_2OH$

4 Z = $CR_2OR_3$ 6
6a R = Cl
6b R = $NO_2$

7 Z = $CR_2R_3$ 9
9a R = Cl
9b R = $NO_2$

10 Z = $CHCO_2Et$
CHCN
$CHSO_2R$ 12
12a R = Cl, X = OH
12b R = $NO_2$, X = OH

13

1b 14 15 16

17 18

19 20

B = absent, $C(R_6R_7)$ or $C(R_8R_9)C(R_6R_7)$

4

21

21a R = $NR_5R_6$

21b R = $OR_5$

22

23

24

25

26

26a R7 = $OR_8$

26b R7 = $NR_8R_9$ 1b 38 39 40 41 42 43 44

NITRO-[2,1-B]IMIDAZOPYRAN COMPOUNDS AND ANTIBACTERIAL USES THEREOF

This is a continuation-in-part of international application PCT/US96/10904 filed Jun. 25, 1996, which is a continuation-in-part of application Ser. No. 08/496,850 filed Jun. 26, 1995, now U.S. Pat. No. 5,668,127.

FIELD OF THE INVENTION

The present invention relates to new nitroimidazole derivatives which are useful in killing pathogenic microbes, to antimicrobial compositions containing the compounds and to the use of the compounds and compositions, alone or in combination with other antimicrobial agents, in the treatment of pathogenic infections, such as infections of mycobacteria, Clostridium, Cryptosporidium or Helicobacter.

BACKGROUND OF THE INVENTION

After a decline in rates of infection over several decades, a disturbing increase in the incidence of tuberculosis (TB) is occurring. Because TB is highly contagious it poses a profound threat to public health. TB bacteria are easily passed from person to person in airborne droplets formed when a person with active TB sneezes or coughs.

Even more alarming has been the rise of multidrug-resistant tuberculosis (MDRTB). Prior to 1984, about 10% of TB bacteria isolated from patients in the United States were resistant to even a single antibacterial drug. In 1984, 52% of patients were infected with *Mycobacterium tuberculosis* (also referred to as tubercle bacilli) resistant to at least one drug, and 32% were resistant to one or more drugs. Outbreaks of MDRTB have been reported in 13 states. Ten percent of the recorded MDRTB cases to date have occurred in previously healthy people whose mortality rate—70 to 90%—has been nearly the same as that of immunosuppressed persons with MDRTB (Snider and Roper, 1992).

The United States Centers for Disease Control (CDC) has released preliminary results of a joint study with the New York State Health Department showing that cases of drug-resistant TB have more than doubled since 1984. CDC data from the first quarter of 1991 show that many of these drug-resistant strains are resistant to both of the frontline TB drugs, rifampin and isoniazid. Outbreaks of MDRTB have occurred in hospitals in Miami and New York City, as well as in the New York State prison system. In one hospital in New York City, the median interval between diagnosis of MDRTB and death was only four weeks. Additional clusters of MDRTB were reported to the CDC in 1990 and 1991 from Mississippi, Missouri, and Michigan.

There are five frontline drugs known to be highly effective against *Mycobacterium tuberculosis* and five second-line drugs that can be used when resistance to one or more of the frontline drugs is detected. Ironically, in the United States, until April 1992, there were shortages of antituberculosis drugs, some of which are crucially needed when resistance to the frontline drugs rifampin and isoniazid is present. These shortages had occurred because several pharmaceutical companies had ceased production of these drugs.

Because of its persistence in the body, the tubercle bacillus is a notoriously difficult pathogen to control. Although bacille Calmette-Guerin (BCG) vaccine protects against severe tuberculosis meningitis and disseminated TB in children, its efficacy against pulmonary TB in adults has varied widely in different parts of the world. Treatment of conventional TB is effective, but expensive, requiring daily treatment with multiple drugs for a minimum of six months. There is a common tendency among TB patients to stop taking their drugs when the drugs begin to have their beneficial effect or to take the medications only intermittently. When this happens, relapses are frequent and very often are caused by drug-resistant tubercle bacilli that have survived the initial course of treatment. The emergence of drug-resistant *M. tuberculosis* is in many ways an index of individual compliance with antituberculosis chemotherapy and of the inability of the health care infrastructure to ensure adequate treatment. Many public health agencies that once could play key roles in this process have had their budgets cut drastically in recent years and hence are unable to perform this crucial service.

MDRTB is extraordinarily difficult to treat, and a majority of patients do not respond to therapy. Total treatment costs for an individual with MDRTB can be as much as 10 times the cost of traditional treatment; the cost of the treatment drugs alone can be as much as 21 times as great.

The preferred treatment for classical TB consists of isoniazid, rifampin, and pyrazinamide. For patients whose tubercle bacilli are thought to be resistant to isoniazid, a fourth drug, ethambutol, is commonly added to the regimen until drug susceptibility results are known. Isolates of tubercle bacilli resistant to both isoniazid and rifampin, now representing about 20% in some cities, require specialized treatment with additional medications, which may include streptomycin and ciprofloxacin for almost two years.

The tubercle bacillus is a slow-growing organism. Three to six weeks are needed to grow the bacteria in the clinical laboratory, and an additional three to six weeks are needed to screen for antibiotic resistance. Such extended laboratory procedures can result in a delay in diagnosis, which means that patients with unrecognized drug-resistant TB may be treated ineffectively and remain infectious for a longer period. In HIV-positive individuals, MDRTB usually causes death within 4 to 16 weeks after being diagnosed, which is often before laboratory tests on drug susceptibility and resistance can be completed.

There is no evidence that mutation rates in *M. tuberculosis* organisms have increased or that increased virulence is to blame for the recent deadly outbreaks of TB. It is likely that drug-resistant forms of tuberculosis arose because of patient noncompliance with the 6- to 12-month regimen of antibiotics required to treat TB. Ineffective treatment regimens also play a role in the rising incidence of TB. To address noncompliance, some states with high TB rates are considering approaches to outreach, such as expanding directly observed therapy (DOT); others may reestablish inpatient facilities similar to the TB sanatoria of the first half of this century. Standard treatment regimens for TB have also been updated. Instead of taking two or three antibiotics, TB patients now take four. Still, as noted earlier, the current shortages of antituberculosis drugs in the United States have made even standard treatment difficult.

A series of nitroimidazo[2,1-b]oxazole derivates was described in Sehgal, K. et al., "Novel Nitroimidazo[2,1-b]oxazole Formation from Reaction of 2,4(5)-Dinitroimidazole with Oxiranes (1)," *J. Heterocyuclic Chem.* 16:1499–1500 (1979). Compounds of this type have the following general formula (I):

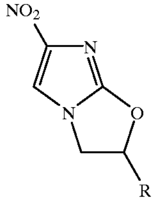

(I)

These compounds were described as potential radiosensitizing agents for use in the radiotherapy of cancer (Agrawal, K. et al., "Potential Radiosensitizing Agents. Dinitroimidazole;" *J. Med. Chem.* 22(5):583–586 (1979); Sehgal, R. et al, "Potential Radiosensitizing Agents. 2. Synthesis and Biological Activity of Derivatives of Dinitroimidazole with Oxiranes," *J. Med. Chem.* 24:601–604 (1981). More recently, certain nitroimidazole compounds were reported to exhibit antimicrobial properties, including antitubercular activity (see, e.g., Nagarajan, K. et al., "Nitroimidazoles XXI. 2,3-dihydro-6-nitroimidazo [2.1-b] oxazoles with antitubercular activity," *Eur. J. Med. Chem.* 24:631–633 (1989). In addition, the compound of formula (I) in which R is ethyl (2-ethyl-5-nitro-2,3-dihydro[2,1-b]imidazo-oxazole, also known as Ceiby-Geigy CGI 17341) has recently been shown to exhibit activity against *Mycobacterium tuberculosis* (Ashtekar, D. et al., "In Vitro and In Vivo Activities of the Nitroimidazole CGI 17341 against *Mycobacterium tuberculosis,*" *Antimicrobial Agents and Chemotherapy,* 37(2):183–186 (1993).

Pseudomembranous colitis (PMC) is a serious intestinal disease marked by severe colonic inflammation, diarrhea, abdominal cramps, and mucosal plaques or pseudomembranes. PMC is caused by the over production of toxigenic *Clostridium difficile* in the gut. *C. difficile* is a spore-forming anaerobe and is the major nosocomial pathogen of PMC. The over growth of *C. difficile* occurs when the bacterial flora of the GI tract has been modified due to extensive use of broad spectrum antibiotics. Two toxins, A and B, are produced by *C. difficile.* The toxins attack membranes or microfilaments of colon cells producing inflammation and necrosis. Toxin A causes intestinal hemorrhage and fluid secretion while toxin B is cytotoxic.

PMC as a subclass of diarrheal disease has become a frequent complication of antibiotic use. PMC normally appears 5–10 days after onset of antibiotic therapy. A watery diarrhea is the most common symptom, occurring in 90–95% of all PMC cases (Aronsson, B. et al., *J. Infect. Dis.* 151:476–481 (1985)). Severe cases of PMC can cause high fever, leukocytosis, dehydration, electrolyte imbalance, and death (see Clostridium difficle: Its role in Intestinal Disease. R. D. Rolfe and S. M. Finegold, Ed., Academic Press Inc., New York (1988), and R. Fekety, ÒAntibiotic-Associated Colitis. Mediguide to Infectious DiseaseÓ Vol. 4, pp. 1–7 (1984)).

Patients at greatest risk include the elderly, debilitated cancer patients, and patients undergoing abdominal surgery. Untreated *C. difficile* produces 10–20% mortality in elderly or chronically debilitated patients (Dosik, G. M. et al., *Am. J. Med.* 67:646–656 (1979)). Worldwide incidence of PMC is unknown due to the lack of appropriate studies. However, in industrialized countries, *C. difficile* is rapidly becoming the most common enteric bacterial pathogen after Campylobacter and Salmonella (Bartlett, J., see Clostridium difficle: Its role in Intestinal Disease. R. D. Rolfe and S. M. Finegold, Ed., Academic Press Inc., New York, pp. 1–13 (1988)).

Antibiotics most frequently used to treat PMC include vancomycin, metronidazole, and bacitracin. Vancomycin is a very expensive treatment, $100–$400 for a ten day course. Relapse rate after vancomycin therapy has been shown in experimental animals (Swannson, B. et. al., *Antimicrobial Agents and Chemotherapy,* 35:1108–1111 (1991) and Bartlett, J. G. et al., *Clin. Infect. Dis.* (S4) S265–72 (1994)). Due to the increase of vancomycin resistant bacteria, the use of vancomycin for *C. difficile* infections may be on the decline. Metronidazole is less effective than vancomycin, however, it is also less expensive. Metronidazole is orally absorbed and may expose patients to potential side effects that are associated with the drug (PHYSICIANS DESK REFERENCE, 48TH EDITION, 1994, pp. 1704–1706). Metronidazole has a relapse rate similar to vancomycin. Bacitracin is an antibiotic polypeptide and is commercially available as a mixture of nine peptides. It is also expensive and no convenient oral dosage form is available.

Organisms of the genus Cryptosporidium are small obligate intracellular coccidian parasites that infect the microvilli epithelial lining of the digestive tract and rarely the respiratory tract. *Cryptosporidium parvum,* which is the most common member of the genus, is the causative agent of Cryptosporidiosis. These organisms are in the same order as the Plasmodium (the Malaria parasite), but the developmental life cycle, transmissibility and diseases are very different. Although recognized and identified as a parasite for a long time, the first cases of human Cryptosporidiosis were reported in 1976. Cryptosporidium is capable of infecting various types of farm and domestic animals as well. This parasite is recognized worldwide as a causative agent of diarrhea. The source of human infections is thought to be through zoonotic transmission (mainly calves, but other animals such as rodents, puppies, and kittens) and through person-to-person contact. However, this mode of transmission alone does not account for the wide-spread transmission, and epidemiological studies have shown that *Cryptosporidium parvum* is a water-borne pathogen. In the Spring of 1993, a massive outbreak of Cryptosporidiosis occurred in the Metropolitan Milwaukee area afflicting an estimated 400,000 persons (the largest single documented outbreak of an infectious disease in North America). This outbreak was linked to the city's water supply.

The most common clinical indications of Cryptosporidium infections are frequent watery diarrhea and low grade fever. Other symptoms include: cramps, nausea, vomiting and weight loss. Both the duration of symptoms and severity of disease and outcome vary according to age and immune status of the patient.

In immuno-competent persons, the infection causes watery diarrhea of a median duration of 10 days (range 1–20), with varying degrees of occurrence of other symptoms. The infection is considered self-limiting, but in children and infants, it has been associated with causing malnutrition, severe morbidity and spread to cause large outbreaks.

In immuno-compromized persons, the duration, severity and outcome of disease depend on the severity and cause of immune deficiency. For example, in certain patients with AIDS, infections with Cryptosporidium causes severe, prolonged diarrheal illness with malnutrition and dehydration and may be a major factor leading to death due to excessive loss of water. Involvement of biliary and respiratory trees can also occur and complicates disease further. For other patients (e.g., persons on steroid therapy), the infection may be cleared upon termination of the immuno-suppressive agent.

The infection begins with the organism colonizing the ileum and jejunum causing impaired digestion and malabsorption due to parasite-induced damage to the villi. The secretory (Cholera-like) diarrhea suggests a toxin-mediated outpouring of fluids into the gut, but no toxins have been documented as yet. Cryptosporidium is associated with diarrheal illness in all areas of the world. It is estimated that the overall prevalence of Cryptosporidium in individuals with diarrhea is 2–2.5% for persons living in industrialized countries and 7–8.5% for persons living in developing countries. The overall prevalence rate reported in various studies in North America has ranged between 0.6%–4.3% (2% in AIDS patients).

There is currently no standard effective therapy for Cryptosporidiosis. As a diarrheal disease, therapy for Cryptosporidiosis relies on relieving symptoms as well as specific therapy, with anti-cryptosporidial drugs and hyper immune globulin. Current treatment in normal hosts is symptomatic. Fluid and electrolyte replacement is the primary importance in management. Non-specific anti-diarrheal agents such as Kaopectate, Loperamide (Immodium), Phenoxylate (Lomotil), and Pepto-Bismol are not consistently effective. To date, specific treatment of Cryptosporidium immune-deficient persons has been also unsuccessful. A number of drugs have been evaluated using animal models and none have shown good promise in eliminating the infection. Immunotherapy using Bovine dialyzable Leukocyte extracts and Passive lacteal immunity using antibodies in hyper immune Bovine colustrum have shown different results.

Several treatment modalities have been tried either in individual cases or in limited scale controlled studies, and have shown various degrees of success. Examples include: Diloxamide furoate and furazolidone (DNA damaging agents Nitrofuran analog anti-Giardia drug), Quinine plus Clindamycin, oral Spiramycin (a macrolide), alpha-difluoromethylornithine (active against other parasites and *P. carinii*), and Interleukin-2.

As noted above, effective treatment of Cryptosporidium infections is lacking. Generally, this has not been a major problem in healthy persons because diarrhea usually lasts for less than 20 days and clinical symptoms usually are resolved spontaneously. However, recent resurgence of large outbreaks have demonstrated an association between this infection and malnutrition, and therapy may be warranted. If a safe and effective therapy were available, most clinicians would tend to treat the infection, regardless of the immune status of the patient (this would be done to prevent progression to more severe disease, and to block transmission to other susceptible hosts). Since most immuno-compromized patients often develop a prolonged, life threatening infection, an effective therapy is needed for this particular patient population.

*Helicobacter pylori* causes chronic gastritis in humans and has been implicated as a pathogenic factor in gastric and duodenal ulcers, gastric carcinoma and non-ulcer dyspepsia. These are important diseases because of their prevalence, their impact on morbidity and mortality and because of their cost to the health system. Diseases associated with *H. pylori* infection are primarily chronic conditions with multifactorial causes, although products which successfully eradicate *H. pylori* infection should greatly reduce the incidence and prevalence of these diseases.

Worldwide sales of anti-ulcer drugs exceed $6.5 billion. *H. pylori*-associated diseases generate enormous amounts of revenue for pharmaceutical firms. The market for GI drugs is currently dominated by histamine H2 receptor antagonists. Consequently, there exists a medical need for novel anti-*H. pylori* agents. The major thrust amongst pharmaceutical firms has been to evaluate existing products. Only two new antibiotics are in development: Abbott's Biaxin which was recently approved for the treatment of *H. pylori* infections and Azithromycin, a related macrolide from Pfizer, has shown promise.

From an economic perspective, antibiotics represent the treatment of choice for therapy of duodenal ulcers. Compared with other options (intermittent or maintenance therapy with H2 antagonists, highly selective vagatomy), antibiotics are relatively cheap and provide the least time spent with an active ulcer.

The major obstacle to successful eradication of *H. pylori* is gaining access to the organism. *H. pylori* is relatively easy to kill in vitro. It is susceptible to acids, bismuth and many antibiotics, but none of these are effective when used for monotherapy in vivo. Eradication rates with monotherapies have rarely exceeded 10%. Successful treatment of *H. pylori* requires an understanding of the physiology of the gastrointestinal sites where the infection resides and the pharmacokinetic nature of the agents used. The bacteria reside under and within gastric mucus, in gastric glands and intracellular spaces, and in the duodenal mucosa. These diverse sites mean that effective delivery of antimicrobial agents by either local or systemic is difficult to achieve. Levels of amoxycillin, bismuth and imipenem/cilastatin in the human gastric mucosa after oral administration have all been shown to exceed the in vitro MIC for the organism, although none of these agents have demonstrated efficacy in vivo. Reasons for this include failure of the drugs to penetrate into all sites of *H. pylori* colonization and inability to maintain adequate bactericidal levels in the mucosa. Failure of drugs like clindamycin, erythromycin and the quinolones may be due to the effect of intragastric pH. In addition, development of resistance occurs rapidly in *H. pylori* and has been documented for fluoroquinolones, nitroimidazoles and macrolides.

A need continues in the art, however, for improved agents that exhibit antimicrobial activity against pathogenic mycobacteria, Clostridium, Cryptosporidium and Helicobacter, and more particularly for agents and their derivatives that may be highly useful in the treatment of MDRTB.

SUMMARY OF THE INVENTION

It has now been surprisingly discovered that pathogenic mycobacteria, and other pathogenic microbes such as Clostridium, Cryptosporidium and Helicobacter, can be controlled in vitro or in vivo by certain nitroimidazole derivatives. Accordingly, the present invention provides methods of inhibiting the growth of pathogenic microbes in vitro and of treatment of pathogenic mycobacterial infections in vivo using dinitroimidazole compounds of the formula (II):

(II)

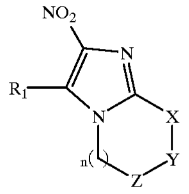

wherein $R_1$ is hydrogen, halogen, loweralkyl, halololoweralkyl, cycloalkyl, heterocycle, substituted heterocycle and heterocyclicalkyl;

X is oxygen, sulfur or $NR_2$, where $R_2$ is hydrogen, loweralkyl, aryl, cycloalkyl, heterocycle, substituted heterocycle, heterocyclicalkyl, $COR_3$ or $SO_2R_4$, $CONR_4R_5$, where $R_3$, $R_4$ and $R_5$ are independently selected from hydrogen, loweralkyl, aryl, alkylaryl, alkoxyalkyl, alkoxyaryl, alkoxyalkoxyaryl, alkylheterocycle, alkoxyheterocycle, substituted heterocycle, heterocycle, alkylarylaryl, arylalkylaryl, $—NR_4COR_5$, $—OCONR_4R_5$, $—NR_4CONR_4R_5$, $OCO_2R_5$, $—NR_4SO_2R_5$, $NR_4SO_2NR_4R_5$, $—NR_4C{=}NR_4NR_5$, and $NR_4R_5$, wherein $R_4$ and $R_5$ may be connected to form a 3–7-membered ring containing from one to three heteroatoms selected from oxygen, nitrogen, or sulfur. The ring can be substituted with substituents independently selected from hydroxy, amino, (C=O), ($SO_2$), alkylamino, arylamino, dialkylamino, alkylarylamino, alkoxy, or halogen.

n is 1, 2 or 3;

Y and Z are independently selected from oxygen, $CH_2$, CO, $CR_4R_5$ or $NR_4$, where $R_4$ and $R_5$ are as defined above;

provided that when n is 2 or 3, the compounds of the invention can be additionally substituted as shown in the following formulas IIa and IIb, respectively:

(IIa)

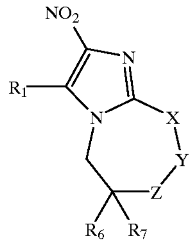

(IIb)

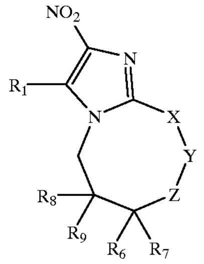

wherein $R_6$, $R_7$, $R_8$ and $R_9$ are independently selected from hydrogen, loweralkyl, aryl, alkylaryl, alkoxyalkyl, alkoxyalkylaryl, alkoxyalkylheterocycle, alkylarylalkylaryl, alkylarylaryl, alkylcycloalkyl, alkoxyaryl, alkylheterocycle, and alkoxyheterocycle;

and the pharmaceutically acceptable salts thereof.

Presently particularly preferred and novel compounds of the invention are provided by the compounds of formula (II) having a backbone structure wherein X is oxygen, according to formula (III):

(III)

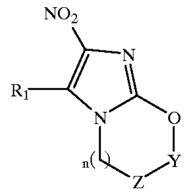

wherein $R_1$, Y, Z and n are as defined above, resulting in the following embodiments IIIa, IIIb and IIIc when n is 1, 2 or 3, respectively:

(IIIa)

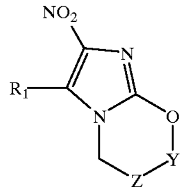

(IIIb)

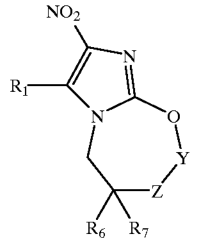

(IIIc)

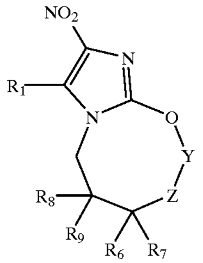

wherein $R_6$, $R_7$, $R_8$ and $R_9$ are as defined above.

In a presently preferred embodiment for the treatment of tuberculosis, the methods and compounds of the invention may be employed alone, or in combination with other anti-*Mycobacterium tuberculosis* agents, such as isoniazid, rifampin, pyrazinamide, rifabutin, streptomycin and ciprofloxacin, to provide new agents for the treatment of tuberculosis, including MDRTB.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

In the accompanying drawings.

DETAILED DESCRIPTION OF THE PREFERRED EMBODIMENT

Figure 1:
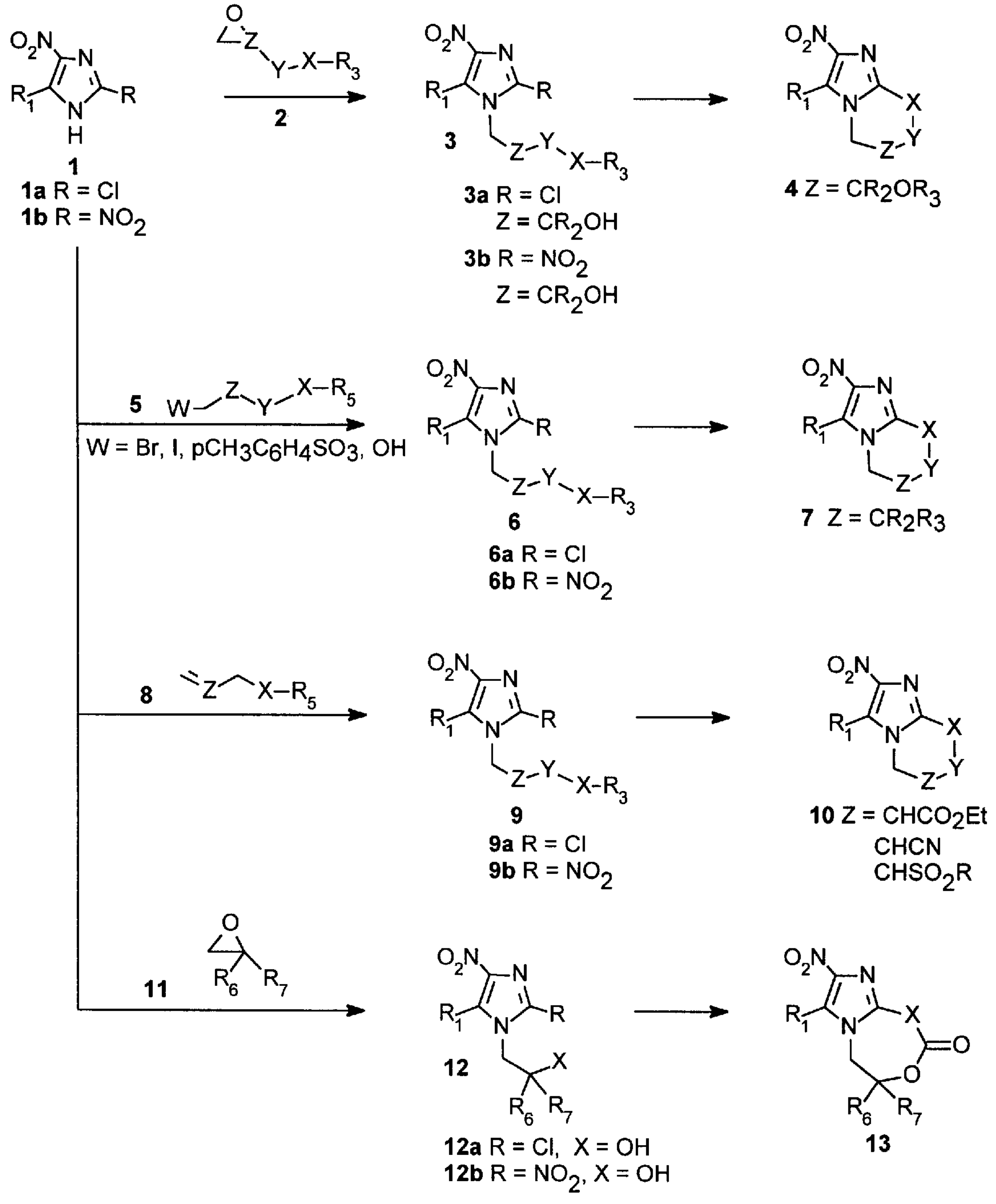
FIG. 1 is a schematic representation of alternative synthesis pathways of compounds of the invention.

In accordance with the present invention, methods are provided for control of pathogenic mycobacteria, either in vitro or in vivo. Thus, in one aspect the present invention provides a method of inhibiting the growth of pathogenic microbes, such as Mycobacterium sp., Clostridium, Crytosporidium and/or Helicobacter, in vitro comprising contacting the microbes with a growth inhibitory amount of a dinitroimidazole compounds of the formula (II):

(II)

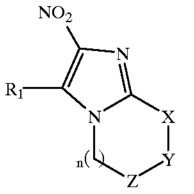

wherein $R_1$ is hydrogen, halogen, loweralkyl, haloloweralkyl, cycloalkyl, heterocycle, substituted heterocycle and heterocyclicalkyl;

X is oxygen, sulfur or $NR_2$, where $R_2$ is hydrogen, loweralkyl, aryl, cycloalkyl, heterocycle, substituted heterocycle, heterocyclicalkyl, $COR_3$ or $SO_2R_4$, $CONR_4R_5$, where $R_3$, $R_4$ and $R_5$ are independently selected from hydrogen, loweralkyl, aryl, alkylaryl, alkoxyalkyl, alkoxyaryl, alkoxyalkoxyaryl, alkylheterocycle, alkoxyheterocycle, substituted heterocycle, heterocycle, alkylarylaryl, arylalkylaryl, $—NR_4COR_5$, $—OCONR_4R_5$, $—NR_4CONR_4R_5$, $OCO_2R_5$, $—NR_4SO_2R_5$, $NR_4SO_2NR_4R_5$, $—NR_4C{=}NR_4NR_5$, and $NR_4R_5$, wherein $R_4$ and $R_5$ may be connected to form a 3–7-membered ring containing from one to three heteroatoms selected from oxygen, nitrogen, or sulfur. The ring can be substituted with substituents independently selected from hydroxy, amino, (C=O), $(SO_2)$, alkylamino, arylamino, dialkylamino, alkylarylamino, alkoxy, or halogen;

n is 1, 2 or 3;

Y and Z are independently selected from oxygen, $CH_2$, CO, $CR_4R_5$ or $NR_4$, where $R_4$ and $R_5$ are as defined above;

provided that when n is 2 or 3, the compounds of the invention can be additionally substituted as shown in the following formulas IIa and IIb, respectively:

(IIa)

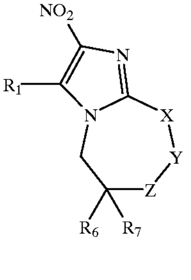

-continued (IIb)

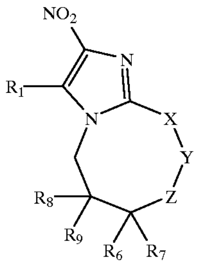

wherein $R_6$, $R_7$, $R_8$ and $R_9$ are independently selected from hydrogen, loweralkyl, aryl, alkylaryl, alkoxyalkylaryl, alkoxyalkylheterocycle, alkylarylalkylaryl, alkylarylaryl, alkylcycloalkyl, alkoxyalkyl, alkoxyaryl, alkylheterocycle, and alkoxyheterocycle;

and the pharmaceutically acceptable salts thereof.

In another aspect, the present invention provides methods of treating human or animal subjects suffering from a pathogenic microbial infection, e.g., tuberculosis, whether of sensitive-strain or multi drug-resistant strain (MDRTB) origin. Thus, the present invention provides a method of treating a human or animal subject in need of such treatment comprising administering to the subject a therapeutically effective amount of a nitroimidazole compound of formula (II), above, either alone or in combination with other antibacterial or antifungal agents.

In another aspect, the present invention provides new antimicrobial nitro-imidazole compounds of the formula (II):

(II)

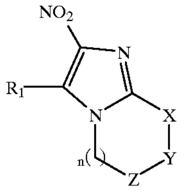

wherein $R_1$ is hydrogen, halogen, loweralkyl, haloloweralkyl, cycloalkyl, heterocycle, substituted heterocycle and heterocyclicalkyl;

X is oxygen, sulfur or $NR_2$, where $R_2$ is hydrogen, loweralkyl, aryl, cycloalkyl, heterocycle, substituted heterocycle, heterocyclicalkyl, $COR_3$ or $SO_2R_4$, $CONR_4R_5$, where $R_3$, $R_4$ and $R_5$ are independently selected from hydrogen, loweralkyl, aryl, alkylaryl, alkoxyalkyl, alkoxyaryl, alkoxyalkoxyaryl, alkylheterocycle, alkoxyheterocycle, substituted heterocycle, heterocycle, alkylarylaryl, arylalkylaryl, $—NR_4COR_5$, $—OCONR_4R_5$, $—NR_4CONR_4R_5$, $—OCO_2R_5$, $—NR_4SO_2R_5$, $—NR_4SO_2NR_4R_5$, $—NR_4C{=}NR_4NR_5$, and $—NR_4R_5$, wherein $R_4$ and $R_5$ may be connected to form a 3–7-membered ring containing from one to three heteroatoms selected from oxygen, nitrogen, or sulfur. The ring can be substituted with substituents independently selected from hydroxy, amino, (C=O), $(SO_2)$, alkylamino, arylamino, dialkylamino, alkylarylamino, alkoxy, or halogen;

n is 1, 2 or 3;

Y and Z are independently selected from oxygen, $CH_2$, CO, $CR_4R_5$ or $NR_4$, where $R_4$ and $R_5$ are as defined above;

provided that when n is 2 or 3, the compounds of the invention can be additionally substituted as shown in the following formulas IIa and IIb, respectively:

(IIa)

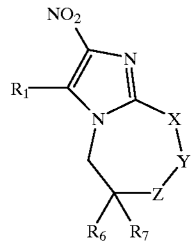

(IIb)

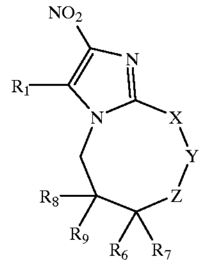

wherein $R_6$, $R_7$, $R_8$ and $R_9$ are independently selected from hydrogen, loweralkyl, aryl, alkylaryl, alkoxyalkylaryl, alkoxyalkylheterocycle, alkylarylalkylaryl, alkylarylaryl, alkylcycloalkyl, alkoxyalkyl, alkoxyaryl, alkylheterocycle, and alkoxyheterocycle;

and the pharmaceutically acceptable salts thereof.

As used above and elsewhere herein the following terms have the meanings defined below:

The term "pathogenic microbes" refers to microbial organisms which do not normally reside in a human or animal host, and which are capable of causing a disease state in the host. Representative examples of pathogenic microbes include, for example, *Mycobacteria tuberculosis, Mycobacteria leprae, Mycobacteria avium* complex, and the like, including multidrug-resistant *M. tuberculosis* strains, *Clostridium difficile, Cryptosporidium parvum* and *Helicobacter pylori.*

The term "acylamino" means an acyl (CO—) radical to which an amino group is appended.

The term "loweralkyl" as used herein refers to branched or straight chain alkyl groups comprising one to ten carbon atoms that are unsubstituted or substituted, e.g., with one or more halogen groups, including, e.g., methyl, ethyl, propyl, isopropyl, n-butyl, t-butyl, neopentyl, trifluoromethyl, pentafluoroethyl and the like.

The term "alkoxy" as used herein refers to RO— wherein R is loweralkyl as defined above. Representative examples of lower alkoxy groups include methoxy, ethoxy, t-butoxy, trifluoromethoxy and the like.

The term "aryl" as used herein refers to a phenyl or a $C_9$- or $C_{10}$-bicyclic carbocyclic ring system having one or more aromatic rings, including naphthyl, tetrahydronaphthyl, indanyl, indenyl and the like. Aryl groups can be unsubstituted or substituted with one, two, three, four or five substituents independently selected from loweralkyl, haloalkyl, alkoxy, aryl, alkoxyaryl and halo.

The term "alkylaryl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylaryl" as used herein refers to an alkylaryl group as previously defined appended to an aryl group. Representative alkylarylaryl groups include 4-benzylphenyl, 3-benzylphenyl, 4-phenethylphenyl and the like.

The term "arylaryl" as used herein refers to an aryl group as previously defined which is appended to an aryl group. Representative arylaryl groups include biphenyl, 4-(1-naphthyl)phenyl, 4-(2-naphthyl)phenyl and the like.

The term "aryloxy" as used herein refers to RO— wherein R is an aryl group. Representative arylalkoxy group include phenyloxy, napthyloxy and the like.

The term "alkoxyaryl" as used herein refers to a lower alkoxy radical to which is appended an aryl group. Representative arylalkoxy group include benzyloxy, phenylethoxy and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "alkylcycloalkyl" as used herein refers to a loweralkyl radical to which is appended a cycloalkyl group. Representative examples of alkylcycloalkyl include cyclopropylmethyl, cyclohexylmethyl, 2-(cyclopropyl)ethyl and the like.

The term "halogen" or "halo" as used herein refers to iodo, bromo, chloro or fluoro.

The term "haloalkyl" as used herein refers to a lower alkyl radical, as defined above, bearing at least one halogen substituent, for example, chloromethyl, fluoroethyl or trifluoromethyl and the like.

The term "heterocycle" as used herein refers to an aromatic ring system composed of 5 or 6 atoms selected from the heteroatoms nitrogen, oxygen, and sulfur. The heterocycle maybe composed of one or more heteroatoms that are either directly connected such as pyrazole or connected through carbon such as pyrimidine. Heterocycles can be substituted or unsubstituted with one, two or three substituents independently selected from amino, alkylamino, halogen, alkyl acylamino, loweralkyl, aryl, alkoxy.

The term "substituted heterocycle" or "heterocyclic group" or heterocycle as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0–2 double bounds and the 6-membered ring has 0–3 double bounds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. Heterocyclics in which nitrogen is the heteroatom are preferred. Fully saturated heterocyclics are also preferred. Preferred heterocycles include: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substituents independently selected from hydroxy, halo, oxo (C═O), alkylimino (RN═, wherein R is a loweralkyl group), amino, alkylamino, dialkylamino, acylaminoalkyl, alkoxy, thioalkoxy, polyalkoxy, loweralkyl, cycloalkyl or haloalkyl. The most preferred heterocyclics include imidazolyl, pyridyl, piperazinyl, azetidinyl, thiazolyl, triazolyl benzimidazolyl, benzothiazolyl, benzoxazolyl and the following:

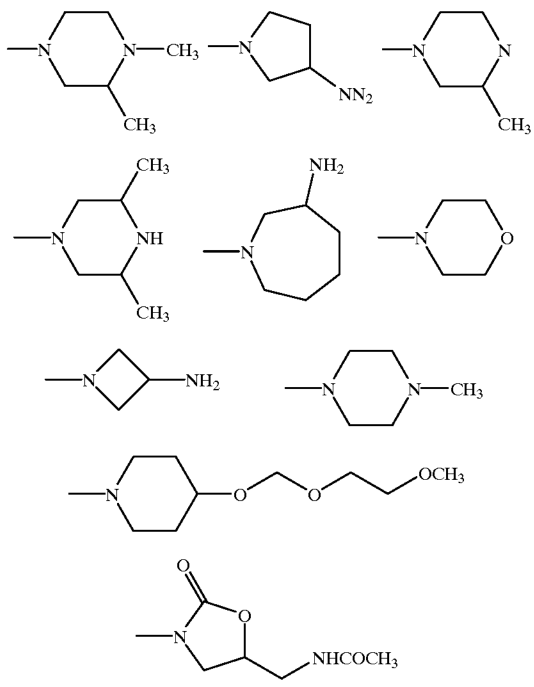

The compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13–30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

Preferred compounds of the invention include compounds of the formula (II) having a backbone structure wherein X is oxygen, according to formula (III):

(III)

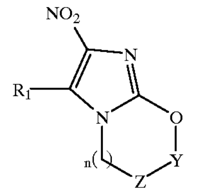

wherein $R_1$, Y, Z and n are as defined above, resulting in the following embodiments IIIa, IIIb and IIIc when n is 1, 2 or 3, respectively:

(IIIa)

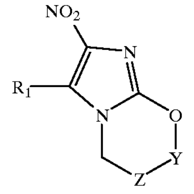

(IIIb)

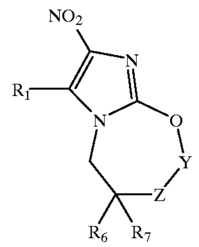

(IIIc)

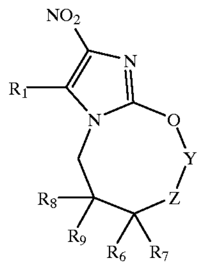

wherein $R_6$, $R_7$, $R_8$ and $R_9$ are as defined above; and the pharmaceutically acceptable salts thereof.

Presently more preferred compounds of the invention include compounds of the formula (IV):

(IV)

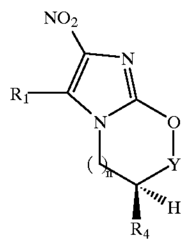

wherein $R_1$, $R_4$, n and Y are as defined above; and the pharmaceutically acceptable salts thereof.

Presently, even more preferred compounds of the invention include compounds of the formula (IVa):

(IVa)

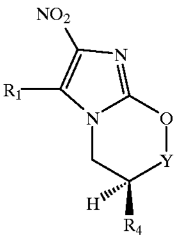

wherein $R_1$, $R_4$ and Y are as defined above; and the pharmaceutically acceptable salts thereof.

The presently most preferred compounds of the invention include compounds of the formula (IVb):

(IVb)

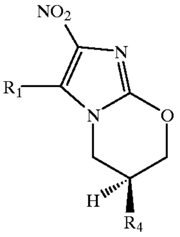

wherein $R_1$ and $R_4$ are as defined above; and the pharmaceutically acceptable salts thereof. Representative compounds of this group include, for example, but are not limited to, 4-trifluoromethorybenzyl carbamate of 3S 3-hydroxy-6-nitro-3,4-dihydro-[2,1b]imidazopyran (PA No. 1343, Example 32), 4-(trifluoromethyl)phenyl carbamate of 3S hydroxy-6-nitro-2H-3,4-dihydro-[2,1b]imidazopyran (PA No. 1327, Example 35), 3S 4-(trifluoromethyl) benzyloxy-6-nitro-2H-3,4-dihydro-[2,1b]imidazopyran (PA No. 636, Example 37), 3S 4-(trifluoromethoxy)benzyloxy-6-nitro-2H-3,4-dihydro-[2,1b]imidazopyran (PA No. 824, Example 41), 4-bromobenzyl carbamate of 3S 3-hydroxy-6-nitro-3,4-dihydro-[2,1b]imidazopyran (PA No. 1324, Example 47), and 4-chlorophenyl urea of 3S 3-amino-6-nitro-3,4-dihydro-[2,1b]imidazopyran (PA No. 1282, Example 48), and the pharmaceutically acceptable salts thereof.

The present invention also relates to the processes for preparing the compounds of the invention and to the synthetic intermediates useful in such processes, as described in detail below.

Figure 2:
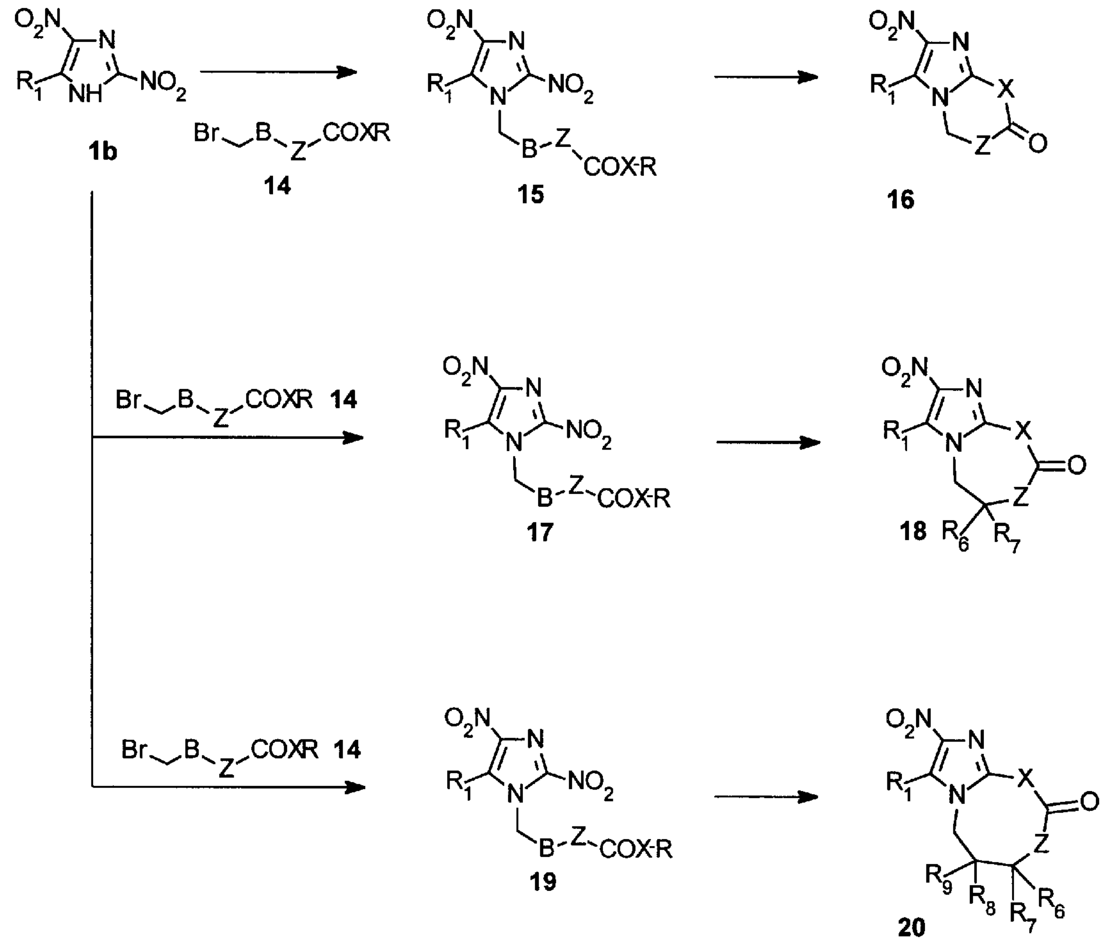
FIG. 2 is a schematic representation of further synthesis pathways of compounds of the invention.

In yet a further aspect of the present invention, pharmaceutical compositions are provided which comprise a compound of the present invention in combination with a pharmaceutically acceptable carrier. In general, the compounds of the invention can be prepared by the processes illustrated in Schemes I (FIGS. 1 and 2), II (FIG. 3), III (FIG. 4) and IV (FIG. 5). According to the reaction Scheme I, functionalized nitroimidazole compounds 4, 7, 10, 13, 16, 18, and 20 are prepared by three methods. The first method involves the alkylation of 2,4-dinitroimidazole (1*b*, $R_1$=H, *Ind. J. of Chem.* 21B:1022–1026 (1982)) or 2-chloro-4-nitroimidazole (1*a*) with epoxides 2 and 11 using a modified procedure of Agrawal et al., (*J. Med. Chem.* 24:601–604 (1981)) in which compounds 1*a* or 1*b* and epoxides 2 or 11 are warmed to 70° C. as a neat solution and kept at 70° C. for several hours. The hydroxy dinitroimidazole or chloronitroimidazole products 3 (Z=$CR_2OH$) and 12 (X=OH) are isolated as crude solids by washing the reaction mixture with diethyl ether and aqueous sodium bicarbonate. The crude hydroxy imidazole 3 ($Z_1$=$CR_2OH$) is protected as an ether derivative selected from but not limited to 2-tetrahydopyranyl (THP), trimethylsilyl (TMS), t-butyldimethylsilyl (TBDMS), acetyl (Ac), benzyl (Bn), and 2,4-dimethoxybenzyl. The second method involves the alkylation of 2-chloro-4-nitroimidazole 1*a* or 2,4-dinitroimidazole 1*b* with an alkyl halide 5 or 14 or alcohol 5 (W=OH) to produce substituted dinitroimidazole or chloronitroimidazole compounds 6, 15, 17 or 19. The third method utilized for the preparation of 1-alkyl-2,4-dinitroimidazole compounds involves reaction of 1 with electron poor olefins such as 8 (Z=CCN, $CCO_2Et$, $CSO_2R$) to give imidazoles 9. Removal of the $R_3$ protecting group from compounds 3, 6, and 9 affords an alcohol (X=OH), amine or amide (X=NR), or a mercaptan (X=SH). When X is a methylene or methine the $R_3$ group maybe present. The bicyclic nitroimidazole compounds 4, 7, 10, 13, 16, 18, and 20 are obtained by reaction of 3, 6, 9, 12, 15, 17, and 19 (X=OH, NHR, SH, CHR, X=OCONHR, Y=CO or $CR_1R_2$) with bases such as sodium hydride, potassium t-butoxide, cesium fluoride, tetrabutylammonium fluoride (TBAF) and the like in an inert and dry organic solvent such as dimethylformamide (DMF), tetrahydrofuran (THF) or dimethoxyethane (DME).

Figure 3:
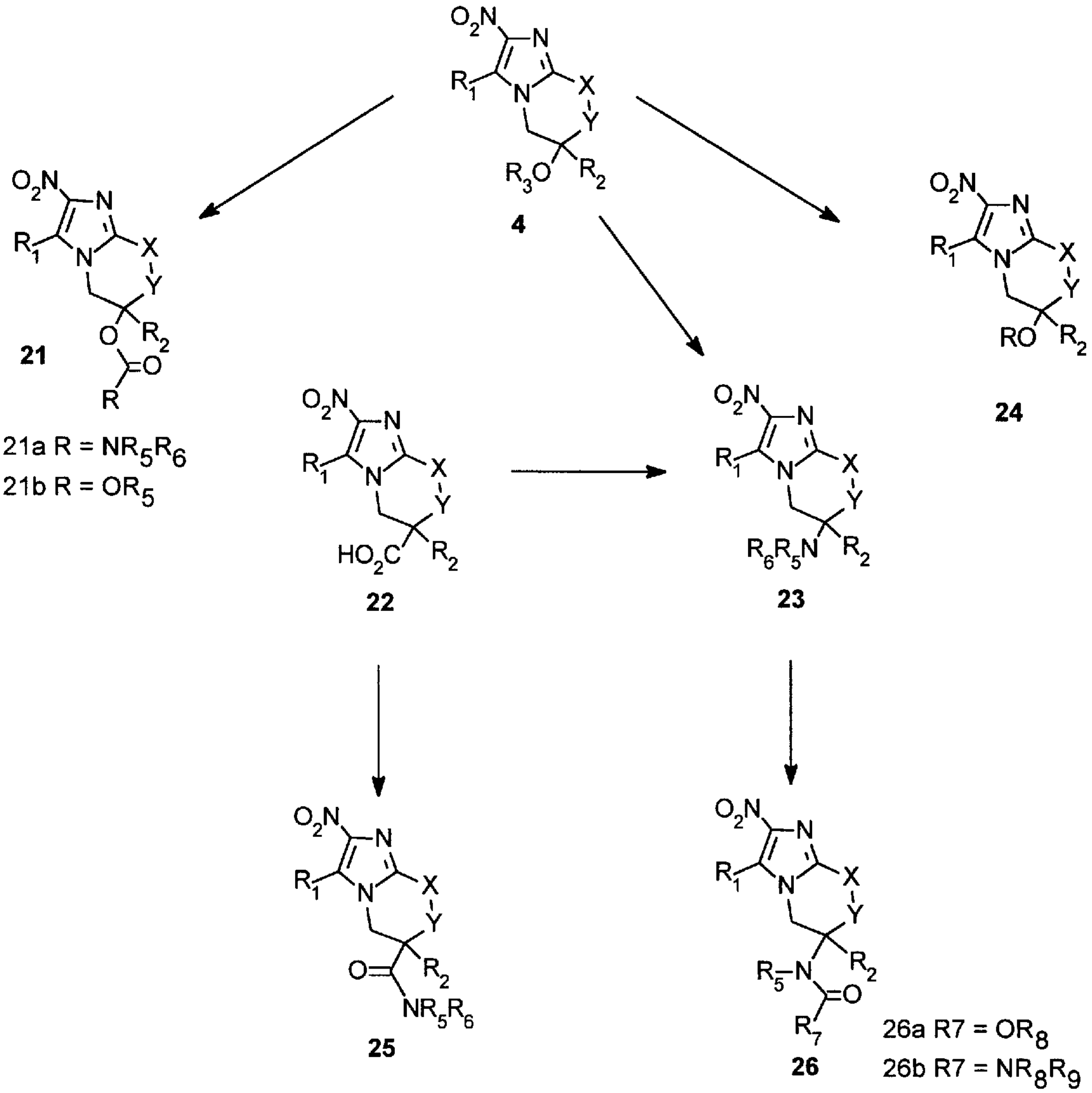
FIG. 3 is a schematic representation of alternative synthesis pathway of compounds of the invention.

The preparation of bicyclic nitroimidazole derivatives are shown in FIG. 3. Deprotection of 4 (for example R=THP) with acetic acid in aqueous THF at room temperature to reflux temperature for several hours gives alcohol 4 ($R_3$=H) which can be reacted with a variety of acylating and alkylating reagents to produce analogs 21*a*, 21*b*, and 24. For example, the carbamate compound 21 is prepared by reacting 4 ($R_3$=H) with carbonyldiimidazole (CDI) and a base such as diazabicycloundecene (DBU), sodium hydride, potassium t-butoxide, sodium bis(trimethylsilyl)amide and the like in an inert and dry solvent. The resulting acylimidazole intermediate 4 ($R_3$=C=Oimidazole) is reacted with a primary or secondary amine to give the carbamate. Alternatively, the carbamate 21*a* can be prepared from 4 ($R_3$=H) and an isocyanate using copper chloride or copper iodide catalyst. The ether analogs 24 are prepared by reacting alcohol 4 ($R_3$=H) with a variety of alkylating reagents selected from but not limited to methyl iodide, octyl iodide, benzyl bromide, 4-benzyloxybenzyl chloride, 4-butylbenzyl bromide and the like with strong bases such as sodium hydride, potassium hydride, sodium bis(trimethylsilyl) amide in a dry aprotic solvent at temperatures between −20° C. to 70° C. The synthesis of the amino and amide derivatives, 23 and 25 or 26, respectively, proceeds through the intermediate, carboxylic acid 22, and alcohol 4. Reaction of 1 with the TBDMS ether of ethyl α-(hydroxymethyl) acrylate (8, R=H, *Org. Synthesis,* 66:220 (1987)) in the presence of a base, for example, sodium ethoxide in ethanol, and deprotection of the silyl ether with tetrabutylammonium fluoride in THF gives the ethyl ester 10 (Z=$CHCO_2Et$, X=O, Y=$CH_2$, FIG. 1). The ester is hydrolyzed using an alkaline base such as sodium hydroxide, lithium hydroxide in water, aqueous ethanol, THF, dioxane and the like. The resulting carboxylic acid 22 is reacted with triethylamine and diphenylphosphorylazide in toluene at 70 to 150° C. to give an isocyanate intermediate. Reaction of an alcohol or amine with the isocyanate gives the carbamate 26*a* ($R_5$=H, $R_7$=$R_8O$) or urea 26*b* ($R_5$=H, $R_7$=$R_8R_9N$), respectively. When the intermediate isocyanate is reacted with t-butanol the product carbamate 26*a* ($R_5$=H, $R_7$=t-BuO) is isolated. Alkylation of the t-butyl carbamate with electrophiles such as an alkyl or alkylaryl halide and the like and deprotection of the Boc (t-butyl carbamate) group with trifluoroacetic acid, or hydrochloric acid gives the secondary amine 23 ($R_5$=H, $R_6$=alkyl, alkylaryl). Alternatively, the Boc at carbamate 26_a_ ($R_5$=H, $R_7$=t-BuO) is reacted with trifluoroacetic acid, or hydrochloric acid to give the primary amine 23 ($R_5$=$R_6$=H) which can be reductively alkylated (RCHO, sodium cyanoborohydride) to give the secondary amine 23 ($R_5$=H, $R_6$=$RCH_2$). A second alkylation of the secondary amine with an electrophile such as an alkyl or alkylaryl halide and the like gives a tertiary amine 23 ($R_5$=$R_6$=alkyl, alkylaryl). Additional reactions that the primary or secondary amine 23 ($R_5$=$R_6$=H or $R_5$=H, $R_6$=alkyl, alkylaryl) undergo include acylation with an acid chloride, sulfonyl chloride, isocyanate, and isothiocyanate to give derivative 26 ($R_5$=H or alkyl, alkylaryl, $R_7$=alkyl, alkylaryl, aryl, heterocycle), 23 $R_5$=H or alkyl, alkylaryl, $R_6$=$SO_2$alkyl, $SO_2$alkylaryl, $SO_2$aryl, $SO_2$heterocycle), 26 ($R_5$=H or alkyl, alkylaryl, $R_7$=NHalkyl, NHheterocycle), and 23 ($R_5$=H or alkyl, alkylaryl, $R_6$=alkylNHC=S, alkylarylNHC=S, arylNHC=S, heterocycleNHC=S). The synthesis of carboxamide derivatives 25 is accomplished by reaction of acid 22 and a primary or secondary amine with a peptide coupling reagent, such as hydroxybenzotriazole (HOBT)/dicyclohexylcarbodiimide (DCC) or 2-[1H-benzotriazole-1-yl]-1,13,3,tetramethyluronium hexafluorophosphate (HBTU) and the like. The peptide coupling reaction may be conducted in a polar aprotic solvent (for example, dimethylformamide and N-methylpyrrolidone (NMP) with a base such as N-methylmorpholine and the like). An alternative synthesis of amine 23 ($R_5$=$R_6$=H) involves the reaction of alcohol 4 ($R_3$=H) with p-toluenesulfonyl chloride in pyridine. The intermediate sulfonate 4 ($R_3$=$pCH_3C_6H_4SO_2$) is reacted with sodium azide. The resulting azide is reduced with 1,3-propanediol and triethyl amine to give amine 23.

Figure 4:
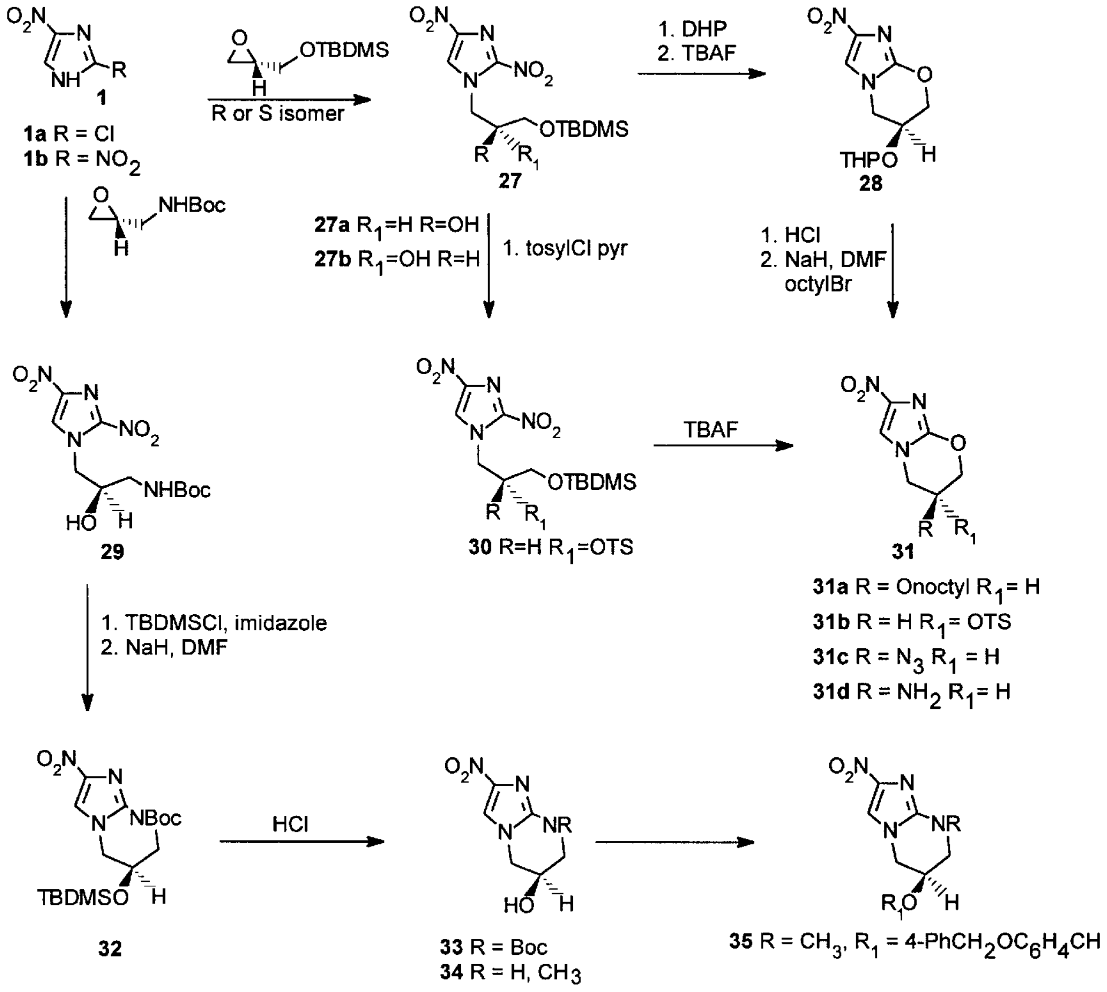
FIGS. 4 and 5 are schematic representations of alternative synthesis pathways of compounds of the invention.
Figure 5:
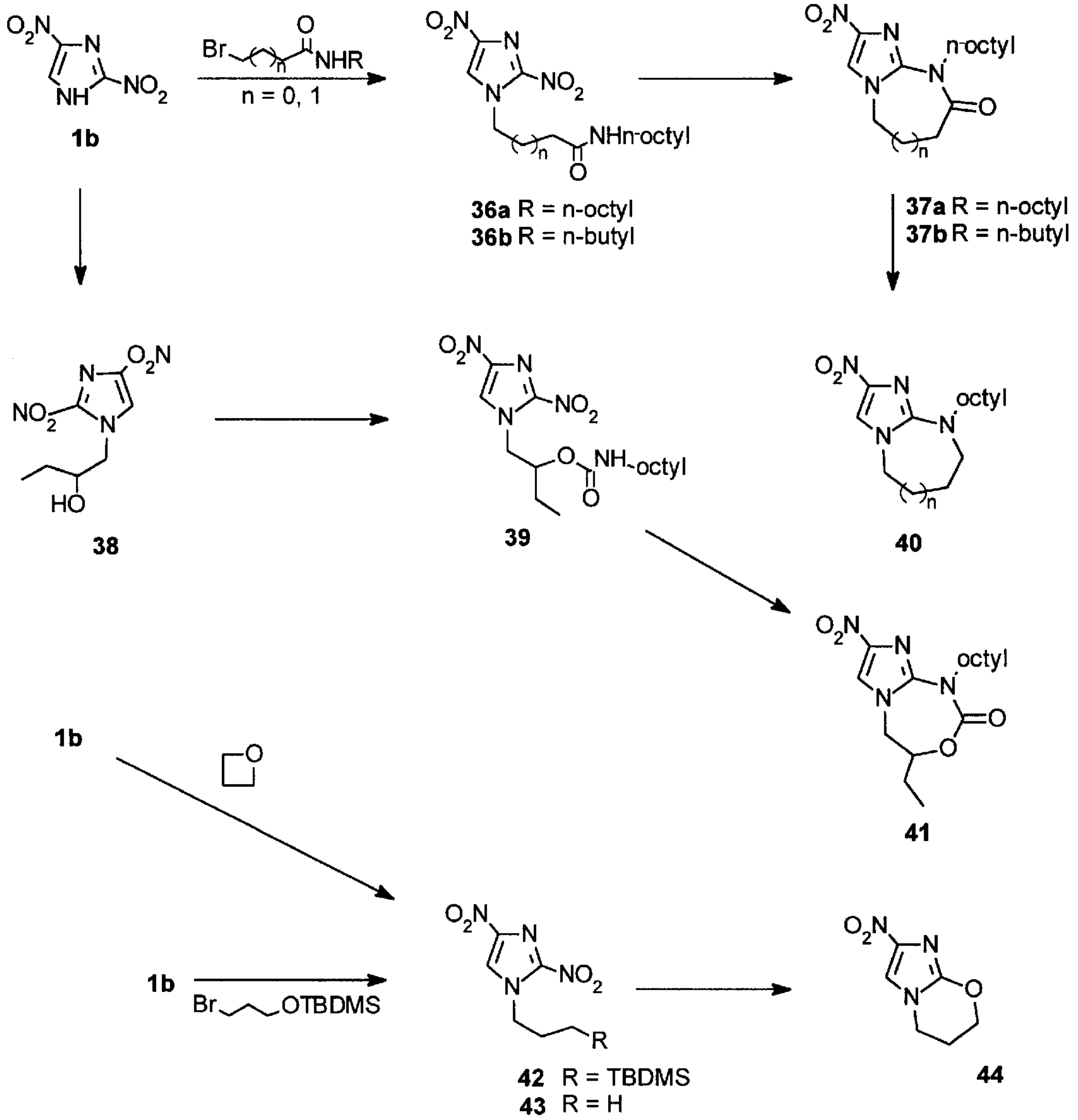

Referring now to FIGS. 4 and 5, specific compounds of the invention are prepared according to the procedures outlined. Reaction of either 2-chloro-4-nitroimidazole 1_a_ or 2,4-dinitroimidazole 1_b_ (1 eq.) with of R- or S-glycidol TBDMS ether (2 eq.) (Example 1) as a neat solution at 70° C. gave the hydroxy imidazole 27_a_ or _b_. Protection of alcohol 27_a_ as its trahydropranyl ether (DHP, p-TsOH) and desilylation of the TBDMS group with tetrabutylammonium fluoride produced the bicyclic nitroimidazole THP ether 28. Deprotection of the THP group was effected using acetic acid in aqueous THF and the resulting alcohol was alkylated with octyl bromide and sodium hydride in DMF at room temperature. The octyl ether 31_a_ was obtained as a white crystalline solid ($[\alpha]^{25}D$=−28.1°). Synthesis of the entiomeric ether series was also acheived and ent-31_a_ was obtained ($[\alpha]^{25}D$=+27.45°). Alternatively, alcohol 27_b_ was tosylated with p-toluenesulfonyl chloride in pyridine to give the tosylate 30. Treatment of the TBDMS ether 30 with TBAF cleaved the silyl group with concominent cyclization to give the cyclic tosylate 31_b_. Reaction of 31_b_ with sodium azide and reduction (1,3-propanediol, triethylamine) gave the amine 31_d_ in good yield. Synthesis of the nitrogen-containing bicyclic nitroimidazole analog 37 was accomplished using a similiar approach. Thus, reaction of 1 with the Boc epoxide gave 29. Protection of alcohol 29 as the TBDMS ether (TBDMSCl, imidazole, DMF) and cyclization of the resulting Boc amino ether with sodium hydride in DMF gave imidazole 32. Both the Boc and TBDMS protecting groups were removed by treating compound 32 with aqueous HCl. The amino alcohol was selectively alkylated (sodium hydride, methyl iodide, DMF) to give the N-methyl derivative 34 (R=$CH_3$) which was alkylated in a second step (sodium hydride, 4-benzyloxybenzyl chloride, DMF, 0° C. to room temperature) affording the aza nitroimidazole compound 35. FIG. 5 illustrates the preparation of cyclic lactams 37, aza analog 40, cyclic carbamate 41 and pyran 44 derivatives. 3-Bromopropionamide and 4-bromobutramides reacted with the sodium salt of 1_b_ in DMF to give the acyclic amides 36. The cyclic amides 37_a_ and 37_b_ were obtained by treating 36_a_ and 36_b_ with sodium hydride in DMF. Reduction of the carbonyl group of 37_a_ was affected with borane in THF at reflux temperature, affording the aza derivative 40 in good yield. The cyclic carbamate 41 was prepared by reacting alcohol 38 with octyl isocyanate in the presense of CuI to give carbamate 39 which was cyclized under basic conditions (sodium hydride, DMF). Finally, the pyranyl nitroimidazole analog 44 was prepared either by alkylation of 1_b_ with the bromo TBDMS ether followed by deprotective cyclization or opening oxetane with 1_b_ in the presense of lithium tetrafluoroborate in THF followed by base (sodium hydride, DMF) induced cyclization of alcohol 43.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful in vitro in inhibiting the growth of pathogenic microbes, and in vivo in human and animal hosts for treating pathogenic microbial infections, including tuberculosis. The compounds may be used alone or in compositions together with a pharmaceutically acceptable carrier.

Total daily dose administered to a host in single or divided doses may be in amounts, for example, from 0.001 to 1000 mg/kg body weight daily and more preferred from 1.0 to 30 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublinigually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids, such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology,* Volume XIV, Academic Press, New York, N.W., p. 33 et seq (1976).

While the compounds of the invention can be administered as the sole active pharmaceutical agent, they can also be used in combination with one or more other agents used in the treatment of pathogenic mycobacterial infections. Representative agents useful in combination with the compounds of the invention for the treatment of *M. tuberculosis* include, for example, isoniazid, rifampin, pyrazinamide, ethambutol, rifabutin, streptomycin, ciprofloxacin and the like. Representative agents useful in combination with the compounds of the invention for the treatment of Clostridium include, for example, vancomycin, metronidazole, bacitracin and the like. Representative agents useful in combination with the compounds of the invention for the treatment of Cryptosporidium include, for example, furoate, furazolidone, quinine, spiramycin, alpha-difluoromthyl-ornithine, interleukin-2 and the like. Representative agents useful in combination with the compounds of the invention for the treatment of Helicobacter include, for example, azithromycin, amoxycillin, clarithromycin and the like.

The above ,compounds to be employed in combination with the nitroimidazole compounds of the invention will be used in therapeutic amounts as indicated in the PHYSICIANS' DESK REFERENCE (PDR) 47th Edition (1993), which is incorporated herein by reference, or such therapeutically useful amounts as would be known to one of ordinary skill in the art.

The compounds of the invention and the other antiinfective agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions which are given at the same time or different times, or the therapeutic agents can be given as a single composition.

The foregoing may be better understood by reference to the following examples, which are provided for illustration and are not intended to limit the scope of the inventive concepts.

EXAMPLE 1

(3S) 1-(2'-Hydroxy-3'-t-butyldimethylsilyloxy)-propyl-2,4-dinitroimidazole

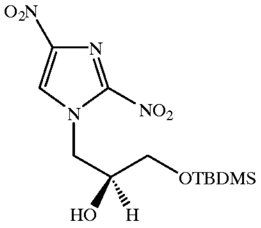

A mixture of 1.93 g (10.5 mmol) of (S)-glycidol tert-butyl dimethylsilyl ether (Liu, H. et al. *J. Org. Chem.,* 57:2471 (1992)) and 1.11 g (7.0 mmol) of 2,4-dinitroimidazole in EtOH (0.5 mL), was heated at 70° C. for 18 hours. The mixture was cooled and directly added to a silica gel column. The product was purified using EtOAc/Hexane (1:4) as the eluant, to give 1.28 g (53%) (3S) 1-(2'-hydroxy-3'-t-butyldimethylsilyloxy)-propyl-2,4-dinitroimidazole as a yellow oil: $^1H$ NMR (DMSO) δ 8.60 (s, 1H), 5.27 (d, 1H), 4.65 (dd, 1H), 4.27 (dd, 1H), 3.96 (m, 1H), 3.60 (dd, 1H), 3.44 (m, 1H), 0.82 (s, 9H), 0.03 (s, 6H); MS 347 $(M+H)^+$.

EXAMPLE 2

3S Tetrahydopyranyloxy-6-nitro-2H-3,4-dihydro-[2-1b]imidazopyran

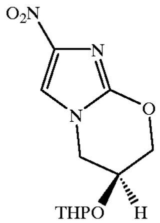

A solution of the compound prepared in Example 1 (1.24 g, 3.6 mmol), 3,4-dihydro-2H-pyran (0.61 g, 7.16 mmol), and 1.35 g (5.37 mmol) of pyridinium p-toluene sulfonate in $CH_2Cl_2$ (20 mL) was stirred for 20 hours at room temperature. The reaction mixture was washed with saturated $NaHCO_3$ and water. The organic layer was dried ($MgSO_4$) and the solvent evaporated. Purification of the residue by silica gel chromatography using hexane:EtOAc (10:1) as the eluant gave 1.21 g of the intermediate THP-protected ether in 79% yield.

To a solution of 1.21 g (2.81 mmol) of the THP ether in dry THF (10 mL) was added 8.4 mL (8.4 mmol) of tetrabutylammonium fluoride (1.0 M solution in THF) dropwise. The reaction mixture was allowed to stir for 1 h, after which the solvent was evaporated. The residue was diluted with $CHCl_3$ and washed with saturated $NaHCO_3$ and water. The organic extracts were dried ($MgSO_4$) and the solvent evaporated. The crude mixture was subjected to column chromatography, using EtOAc:MeOH (97:3) as the eluant, giving 0.55 g (73%) of the title compound: mp 138–139° C.; $^1H$ NMR ($CDCl_3$) δ 7.42 (s, 1H), 4.85 (s, 1H), 4.10–4.60 (m, 4H), 3.54–3.87 (m, 2H), 1.58 (m, 6H); MS 431 $(M+H)^+$.

EXAMPLE 3

3S Hydroxy-6-nitro-2H-3,4-dihydro-[2-1b] imidazopyran

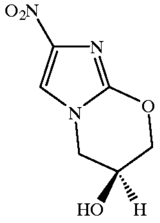

A THF (32 mL) solution of 4.06 g (15 mmol) of the THP ether prepared in Example 2, water (16 mL), and acetic acid (64 mL) was heated at 45° C. for 18 h. The reaction mixture was concentrated and the residue was recrystallized from boiling MeOH to give 2.18 g (79%) of the title compound: mp 220° C. (dec.); $^1H$ NMR (DMSO) δ 8.07 (s, 1H), 5.69 (s, 1H), 4.17–4.39 (m, 4H), 3.98 (d, 1H); MS 186 $(M+H)^+$.

EXAMPLE 4

3S n-Octyloxy-6-nitro-2H-3,4-dihydro-[2-1b] imidazopyran

General Procedure for the Alkylation of Alcohol 4 ($R_3$=H) with Alkyl Halides

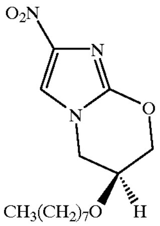

To a DMF (7 mL) solution of the alcohol prepared in Example 3 (1.03 g, 5.55 mmol) cooled to 0° C., was added 0.26 g (6.66 mmol) of NaH (60% in oil). After 0.5 h, 1.03 mL (5.68 mmol) of 1-iodooctane was added and the reaction mixture was stirred at room temperature for 20 h. The reaction was quenched with water and extracted with EtOAc. The organic extracts were dried ($MgSO_4$) and the solvent evaporated. The residue was subjected to column chromatography (hexane:EtOAc) to give 0.49 g (30%) of the title compound: mp 108–109° C.; $[\alpha]^{25}D$ ($CHCl_3$, c=0.1)=−28.1°; $^1H$ NMR ($CDCl_3$) δ 7.41 (s, 1H), 4.55 (dd, 1H), 4.00–4.35 (m, 4H), 3.56 (m, 2H), 1.59 (m, 4H), 1.25 (br s, 8H), 0.87 (m, 3H); MS 298 $(M+H)^+$.

Anal. calcd. for $C_{14}H_{23}N_3O_4$: C, 56.55; H, 7.80; N, 14.13. Found: C, 56.66; H, 7.97; N, 14.00.

EXAMPLE 5

(3R) 1-(2'-Hydroxy-3'-t-butyldimethylsilyloxy)-propyl-2,4-dinitroimidazole

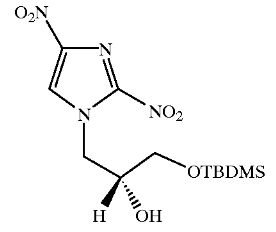

Using the procedure described in Example 1 and substituting (R) gylcidol t-butyldimethylsilyl ether for (S) gylcidol t-butyldimethylsilyl gave (3R) 1-(2'-hydroxy-3'-t-butyldimethylsilyloxy)propyl-2,4-diitroimidazole. $^1H$ NMR ($CDCl_3$) δ 0.13 (s, 6 H), 0.94 (s, 9 H), 3.07 (d, 1 H), 3.75 (d, 2H), 4.13 (m, 1H), 4.53 (dd, 1H), 4.85 (dd, 1H), 8.11(s, 1H); $^{13}C$ NMR ($CDCl_3$) δ 19.21, 26.77, 54.78, 65.02, 70.90, 125.96.

EXAMPLE 6

3R-Tetrahydopyranyloxy-6-nitro-2H-3,4-dihydro-[2-1b]imidazopyran

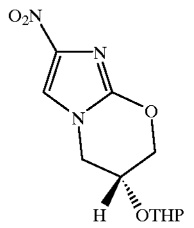

The title compound was prepared using the procedure outlined in Example 2 and substituting the alcohol prepared in Example 5 for the alcohol prepared in Example 1 gave the cyclic THP ether: mp 145–146° C.; $^1H$ NMR (DMSO) δ 1.43 (m, 4 H), 1.65 (m, 2H), 3.49 (m, 1H), 3.63 (m, 1H), 4.18–4.70 (m, 5H), 4.90 (m, 1H), 8.02, 8.05 (ss, 1H); $^{13}C$ NMR (DMSO) δ 20.36, 20.25, 26.21, 26.25, 31.54, 31.61, 47.87, 49.61, 63.25, 63.43, 65.58, 65.72, 69.33, 71.44, 98.29, 98.45, 119.38, 119.45, 148.57.

EXAMPLE 7

3R-Hydroxy-6-nitro-2H-3,4-dihydro-[2-1b]imidazopyran

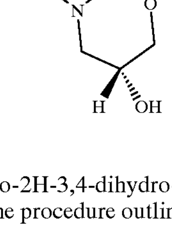

3R-hydroxy-6-nitro-2H-3,4-dihydro-[2-1b]imidazopyran was prepared using the procedure outlined in Example 3 and substituting the THP ether from Example 6 for the THP ether prepared in Example 2: mp 208° C. (decomposed); $^1H$ NMR (DMSO) δ 3.96 (d, 1H), 4.16–4.43 (m, 4H), 5.68 (d, 1H), 8.06 (s, 1H); $^{13}C$ NMR (DMSO) δ 50.70, 60.52, 72.22, 119.53, 143.58, 148.62.

EXAMPLE 8

3R n-Octyloxy-6-nitro-2H-3,4-dihydro-[2-1b]imidazopyran

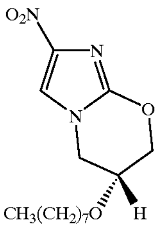

3R-n-octyloxy-6-nitro-2H-3,4-dihydro-[2-1b]imidazopyran was prepared using the general alkylation procedure outlined in Example 4 and the product from Example 8: mp 104–106° C.; $[\alpha]^{25}D$ ($CHCl_3$, c=1)+27.45°; $^1H$ NMR (DMSO) δ 0.83 (t, 3H), 1.25 (m, 12H), 1.44 (m, 2H), 3.53 (q, 2H), 4.08 (q, 1H), 4.18 ppm (d, 2H), 4.49 (q, 2H), 8.03 (s, 1H); $^{13}C$ NMR (DMSO) δ 15.35, 23.51, 26.94, 30.13, 30.50, 32.65, 48.07, 67.92, 69.37, 69.46, 119.38, 143.53, 148.57; MS 298 (M+H).

Anal. calcd. for $C_{14}H_{23}N_3O_4$: C, 56.55; H, 7.80; N, 14.13. Found: C, 56.37; H, 7.86; N, 13.97.

EXAMPLE 9

1-(2'-Hydroxy-3'-N-tert-butyloxycarbonyl)propyl-2,4-dinitroimidazole

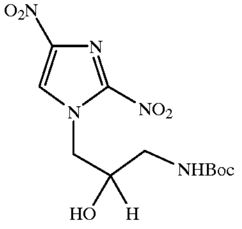

N-(tert-butyloxycarbonyl)allyl amine epoxide

A solution of 5.72 gram (0.1 mol) of allylamine was added dropwise to a solution of 130 mL freshly distilled tetrahydrofuran (THF) and 28.4 gram (0.13 mol) di-tert-butyl dicarbonate under $N_2$ at room temperature. After 3 h the solvent was removed by rotary evaporation and the Boc amine was obtained as a clear oil: $^1H$ NMR ($CDCl_3$) δ 5.91–5.78 (m, 1H), 5.21–5.10 (m, 2H), 4.65 (broad s, 1H), 3.75 (broad s, 2H), 1.45 (s, 9H), indicated desired product was synthesized.

To the crude N-(tert-butyloxycarbonyl)allyl amine in 700 mL of dichloro-methane was added 63 g (0.44 mol) of anhydrous sodium phosphate dibasic and 84 g (0.489 mol) m-chloroperbenzoic acid. The reaction was stirred mechanically for 24 H and quenched with saturated sodium bicarbonate and saturated sodium thiosulfate ($Na_2S_2O_3$) and extracted three times of dichloromethane. The combined organic extracts were dried over magnesium sulfate and concentrated under reduced pressure. Chromatography on silica gel eluting with $CH_3OH$:$CHCl_3$ (1:4) gave N-(tert-butyloxycarbonyl)allyl amine epoxide in 60% yield (10.3 g): $^1$H NMR ($CDCl_3$) δ 4.95 (broad s, 1H), 3.57–3.50 (broad m, 1H), 3.26–3.15 (m, 1H), 3.09 (m, 1H), 2.79–2.76 (t, 1H, J=4.2 Hz), 2.60–2.58 (dd, 1H, J=2.7, 4.8 Hz).

1-(2'-hydroxy-3'-N-tert-butyloxycarbonyl)-propyl 2, 4-dinitroimidazole

A mixture of 2,4-dinitroimidazole (158 mg, 1 mmol) and N-(tert-butyloxycarbonyl)allyl amine epoxide (885 mg, 5 mmol) were stirred under $N_2$ for 19 h at room temperature. Chromatography on silica gel using acetone:hexane (1:2) gave the title compound in 41% yield: $^1$H NMR ($CDCl_3$) δ 8.21 (s, 1H), 5.49 (broad s, 1H), 4.85 (d, 1H, J=13.2 Hz), 4.55–4.53 (m, 2H), 4.15 (broad s, 1H), 3.37 (broad m, 2H), 1.41 (s, 9H); MS $(M+H)^+$ 332.

EXAMPLE 10

N-(tertButylcarbonyloxy) 3S-tert-butyldimethylsilyloxy-6-nitro-1,2,3,4-tetrahydro-[2-1b]imidazopyrimidine

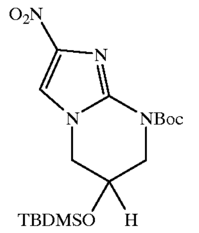

1-(2'-hydroxy-3'-N-tert-butyloxycarbonyl)-propyl 2, 4-dinitroimidazole TBDMS Ether To a mixture of the imidazole compound prepared in Example 9 (1.32 g, 34.3 mmol) in 30 mL of dry dimethyl formamide (DMF) and 1.82 g (5.5 mmol) of the compound prepared in Example 9 was added a solution of 2.20 g (14.6 mmol) of tert-butyldimethylsilyl chloride in 20 mL dry DMF. After 48 h, an equal volume of ether was added and the mixture was washed three times with 0.5 M HCl, two times with saturated sodium bicarbonate and once with brine. The organic solution was dried over anhydrous sodium sulfate, filtered, and concentrated under reduced pressure. Chromatography on silica gel using acetone:hexane (1:4) gave the title compound in 93% yield: mp 47.0–49.5° C.; $^1$H NMR ($CDCl_3$) δ 8.01 (s, 1H), 4.83–4.78 (m, 2H), 3.22–3.17(m, 1H), 1.47(s, 9H), 0.85(s, 9H), 0.04(s, 3H), −0.24(s, 3H).

N-tert-butylcarbonyloxy 3S-tert-butyldimethylsilyloxy-6-nitro-1,2,3,4-tetrahydro-[2-1b]imidazopyrimidine To a solution of 5.11 g (11.5 mmol) of TBDMS ether prepared in Example 10 in 100 mL of dry DMF cooled at 0° C. was added 1.0 g (25 mmol, 60%) sodium hydride in portions. Once addition was completed, an additional 15 min at 0° C. was allowed before the reaction mixture was warmed slowly to room temperature. Four hours later, the reaction was quenched with water, the mixture was extracted with ether:toluene (1:1). The combined organic layers were dried, filtered, and evaporated. The crude residue was purified by silica gel chromatography (acetone:hexane, 1:4) to give the title compound in 51% yield: mp 59.5–61.3° C.; $^1$H NMR ($CDCl_3$) δ 7.52 (s, 1H), 4.37–4.33 (m, 1H), 4.19–4.14 (dd, 1H, J=3.55, 12.88 Hz), 4.12–4.05 (qd, 1H, J=1.63, 4.75, 13.43 Hz), 3.91–3.86 (m, 1H), 3.57–3.52 (dd, 1H, J=1.63, 13.42 Hz), 1.47 (s, 9H), 0.77 (s, 9H), 0.05 (s, 3H), 0.04 (s, 3H).

EXAMPLE 11

3R-Hydroxy-6-Nitro-1,2,3,4-tetrahydro-[2-1b] imidazopyrimidine

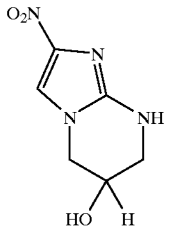

To a solution of TBDMS ether (21.2 mg, 49 mmol) prepared in Example 10 in 5 ml of THF vias added 1 ml of 2N HCl. After stirring at room temperature for 18 h, the reaction mixture was concentrated to dryness, dissolved in $CHCl_3$, and was purified on a silica gel column ($CH_3OH$:$CH_2Cl_2$ 1:4) to give 9.2 mg (85.0% yield) of 3R-hydroxy-6-nitro-1,2,3,4-tetrahydro-[2-1b] imidazopyrimidine as a yellow solid: mp 122° C. (decomposed); $^1$H NMR ($D_2O$) δ 8.05 (brs, 1H), 4.51(m, 1H), 4.20 (brs, 2H), 3.55 (brs, 2H).

EXAMPLE 12

3R-Hydroxy-1-methyl-6-Nitro-1,2,3,4-tetrahydro-[2-1b]imidazopyrimidine

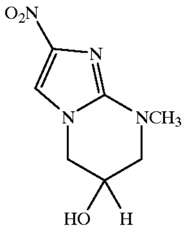

A DMF solution of the amino alcohol prepared in Example 11 is cooled to 0° C. and 1 equivalent of sodium hydride is added. The reaction mixture is stirred for 10 min, 2 equivalents of methyl iodide are added and the reaction mixture is warmed to room temperature and stirred an additional 1 h. Water is added, and 3R-hydroxy-1-methyl-6-nitro-1,2,3,4-tetrahydro-[2-1b]imidazopyrimidine is obtained by chloroform extraction.

EXAMPLE 13

3R-4-Benzyloxybenzyloxy-1-methyl-6-nitro-1,2,3,4-tetrahydro-[2-1b]imidazopyrimidine

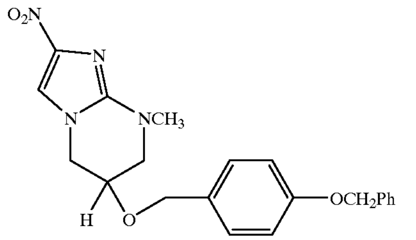

The general alkylation procedure described in Example 4 is followed and substituting the alcohol prepared in Example 12 for the alcohol prepared in Example 3, and substituting 4-benzyloxybenzyl chloride for n-octyl iodide gives 3R-4-benzyloxybenzyloxy-1-methyl-6-nitro-1,2,3,4-tetrahydro-[2-1b]imidazopyrimidine.

EXAMPLE 14

Octyl 4-(2,4-dinitroimidazo-1-yl)butramide

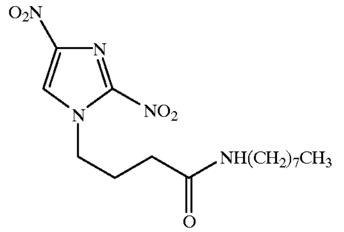

50–60% Sodium hydride (173 mg, 4.3 mmol) was added to a solution of 682 mg (4.3 mmol) of 2,4-dinitroimidazole in 4 mL of dry DMF. The mixture was stirred for 10 min at room temperature and 1 g (3.6 mmol) of N-octyl 4-bromobutyramide in 2 ml dry DMF was added. The temperature of the reaction mixture was increased to 90° C. and the mixture was stirred for 18 h. The reaction mixture was quenched with 100 mL of cold 0.005 N HCl and extracted with ethyl acetate. The organic layer was washed with aqueous sodium bicarbonate, water and dried over anhydrous magnesium sulfate. The solvent was removed and the residue was purified on a silica gel column (hexane:ethyl acetate, 2:3) to give 1.04 g of octyl 4-(2,4-dinitroimidazo-1-yl)butramide in 81% yield. $^1$H NMR ($CDCl_3$) δ 0.80 (t, 3H), 1.19 (m, 12H), 1.41 (m, 2H), 2.23 (m, 4H), 3.13 (m, 2H), 4.64 (t, 2H), 6.08 (t, 2H), 8.15 (s, 1H); $^{13}$C NMR ($CDCl_3$) δ 15.02, 23.58, 26.67, 27.91, 30.16, 30.20, 30.50, 30.55, 32.73, 32.82, 40.72, 51.97, 125.62, 142.17, 144.10, 171.85; MS 356.1(M+H)$^+$.

EXAMPLE 15

Nitroimidazole Octyl Lactam

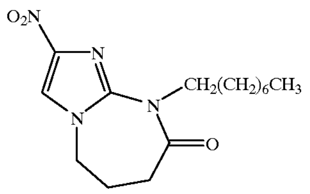

Sodium hydride 148 mg (3.66 mmol) was suspended in 30 mL of dry DMF and 650 mg (1.83 mmol) of the amide prepared in Example 14 in 10 mL dry DMF was added dropwise. The dark blue solution was stirred overnight at room temperature, and 100 mL of 0.005 N HCl was added. The product was isolated by ethyl acetate extraction. The organic extracts were washed with sodium bicarbonate, water, and dried ($MgSO_4$). After removal of the solvent, the residue was purified by silica gel column chromatography (hexane:ethyl acetate, 2:3). The cyclic amide was obtained in 36% yield (204 mg). A sample was recrystallized from ethyl acetate/hexane to give the amide as light yellow needles: mp 92–93° C.; $^1$H NMR ($CDCl_3$) δ 0.86 (t, 3H), 1.24 (m, 10H), 1.57 (m, 2H), 2.42 (m, 2H), 2.48 (t, 2H), 3.94 (t, 2H), 4.13 (t, 2H), 7.73 (s, 1H); $^{13}$C NMR ($CDCl_3$) δ 15.04, 23.56, 27.73, 28.12, 29.53, 30.11, 32.70, 33.76, 45.46, 47.92, 118.94, 144.16, 171.38; MS 309.1 (M+H)$^+$.

EXAMPLE 16

Nitroimidazole Octyl Azapine

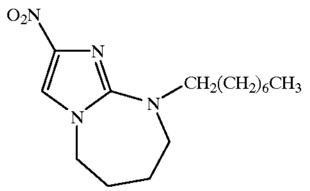

A solution of 0.2 mL (0.2 mmol) 1.0 M borane in 5 mL of THF cooled in an ice-water bath was added 31 mg (0.1 mmol) of the amide prepared in Example 15. The mixture was heated at reflux temperature for 1.5 h and cooled to room temperature. Decomposition of excess borane and borane complex was effected by the dropwise addition of concentrated HCl in water. After washing the aqueous HCl solution to remove neutral compounds, the water layer was treated with sodium bicarbonate and extracted with ethyl acetate. The extracts were dried over magnesium sulfate and the solvent concentrated. The product was purified by silica gel chromatography (hexane:ethyl acetate, 4:1) to give 10 mg of the reduced amide in 33%. $^1$H NMR ($CDCl_3$) δ 0.86 (t, 3H), 1.24 (m, 10H), 1.57 (m, 2H), 1.88 (m, 2H), 3.06 (t, 3H), 3.40 (t, 2H), 3.94 (t, 2H), 7.55 (s, 1H); MS 296.1 (M+H)$^+$.

EXAMPLE 17

N-Octyl Carbamate of 1-(2-hydroxybutyl)-2,4-dinitroimidazole

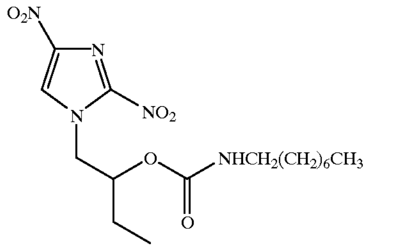

To a heterogeneous mixture of 1-(2'-hydroxybutyl)-2,4-dinitroimidazole (500 mg, 2.17 mmol, *Eur. J. Med. Chem.* 24:631–633 (1989)) and 258 mg (2.60 mmol) of CuI in 10 mL of dry DMF was added 767 μL (4.34 mmol) of octyl isocyanate. The mixture was stirred for 2 h, diluted with 40 mL of ethyl ether and the organic solution was washed with water, dried over magnesium sulfate and concentrated. The crude product was purified by chromatography on silica gel (hexane:ethyl acetate, 6:1) to give 502 mg (60%) of n-octyl carbamate. $^1$H NMR ($CDCl_3$) δ 0.86 (t, 3H), 1.11 (t, 3H), 1.28 (m, 10H), 1.40 (m, 2H), 1.75 (m, 2H), 3.05 (m, 2H), 4.42 (q, 1H), 4.75 (t, 1H), 4.90 (q, 1H), 5.10 (m, 1H), 7.88 (s, 1H); $^{13}$C NMR ($CDCl_3$) δ 9.32, 14.01, 22.54, 25.10, 26.54, 29.06, 29.63, 31.69, 40.04, 41.08, 54.28, 72.65, 124.14, 155.20; MS 386 (M+)

EXAMPLE 18

Nitroimidazole Octyl Cyclic Carbamate

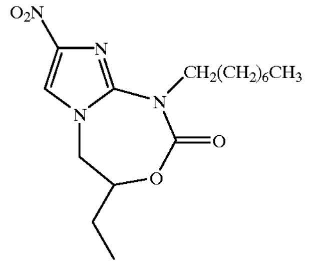

A solution of the compound prepared in Example 17 (500 mg, 1.30 mmol) in 5 mL dry DMF and 50–60% sodium hydride (78 mg, 1.95 mmol) was stirred at room temperature for 1 h. The reaction was quenched with 20 mL of 0.05 N hydrochloric acid and extracted with ethyl acetate. The ethyl acetate extracts were washed with sodium bicarbonate, water and concentrated. The residue was purified by silica gel chromatography (hexane:ethyl acetate, 3:1) to give 260 mg of the cyclized carbamate (59% yield): mp 107–109° C.; $^1$H NMR ($CDCl_3$) δ 0.90 (t, 3H), 1.15 (t, 3H), 1.26 (m, 10H), 1.67–1.95 (m, 4H), 3.95–4.35 (m, 4H), 4.62 (m, 1H), 7.65 (s, 1H); $^{13}$C NMR ($CDCl_3$) δ 9.48, 14.02, 22.55, 26.23, 26.62, 27.70, 29.06, 29.10, 31.68, 49.41, 50.54, 80.50, 117.59, 152.45; MS 338 (M+), 292.2 (M-$NO_2$).

EXAMPLE 19

4-Benzyloxybenzyl Carbamate of 3R-Hydroxy-6-nitro-2H-3,4-dihydro-[2-1b]imidazopyran

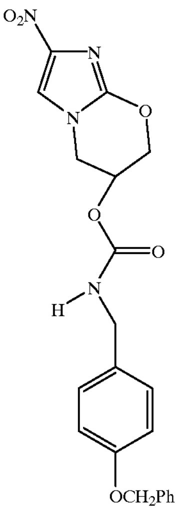

Using the procedure in Example 4, and substituting 1,1-carbonyldiimidazole for 1-iodooctane gave 13 mg (9% yield) of the acylimidazole: $^1$H NMR (DMSO) δ 8.05 (s, 1H), 7.64 (s, 1H), 7.01 (s, 2H), 5.36 (s, 1H), 4.61 (m, 2H), 4.37 (m, 2H).

To a solution of the acylimidazole (1 eq.) in dry THF, 4-benzyloxybenzylamine (1.1 eq., Pandey, G. D. et al., *Pol. J. Chem.* 54:763 (1980)) is added. After the reaction is complete, the 4-benzyloxybenzyl carbamate of 3R-hydroxy-6-nitro-2H-3,4-dihydro-[2-1b]imidazopyran is obtained.

EXAMPLE 20

3R Carboethoxy-6-nitro-2H-3,4-dihydro-[2-1b] imidazopyran

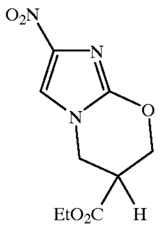

A solution of 2,4-dinitroimidazole (1 eq.), the TBS ether of ethyl α-(hydroxymethyl)acrylate (1.1 eq., *Org. Syn.* 66:220 (1987)) and sodium ethoxide in ethanol is stirred at room temperature. Workup in the usual manner gives the product. Cyclization of the TBDMS ether intermediate is effected by reaction with tetrabutylammonium fluoride as previously described.

EXAMPLE 21

3R-Carboxylate-6-nitro-2H-3,4-dihydro-[2-1b] imidazopyran

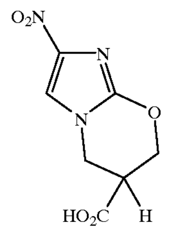

A solution of the ester prepared in Example 20 and (1 eq.) of sodium hydroxide in EtOH is stirred at room temperature. Addition of aq. HCl gives 3R-carboxylate-6-nitro-2H-3,4-dihydro-[2-1b]imidazopyran.

EXAMPLE 22

4-Benzyloxybenzylamine Amide of 3R-Carboxylate-6-nitro-2H-3,4-dihydro-[2-1b] imidazopyran

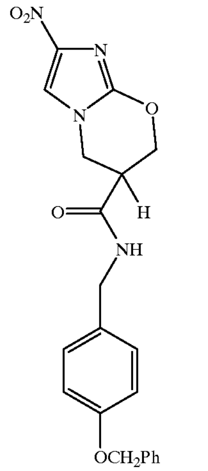

To a solution of the carboxylic acid prepared in Example 21 in DMF is added HBTU (2 eq.), 4-benzyloxybenzyl amine (1.1 eq.), and N-methyl morpholine (NMM, 1.5 eq.). The 4-benzyloxybenzyl amine amide of 3R-carboxylate-6-nitro-2H-3,4-dihydro-[2-1b]imidazopyran is obtained after workup and purification.

EXAMPLE 23

4-Benzyloxybenzamide of 3R-Amino-6-nitro-2H-3,4-dihydro-[2-1b]imidazopyran

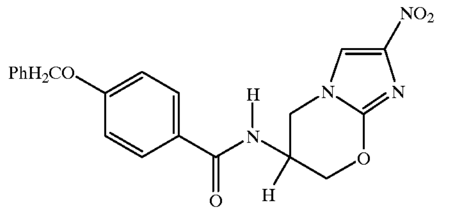

A solution of 3R-carboxylate-6-nitro-2H-3,4-dihydro-[2-1b]imidazopyran (Example 21, 1 eq.), triethylamine (1 eq.), diphenylphosphoryl azide (1 eq.) in toluene is heated at 80° C. for 4 h, cooled and t-butanol is added. The reaction is warmed to 70° C. for an additional 1 h. Workup in the standard fashion gives the Boc amine. Deprotection of the Boc group (trifluoroacetic acid:dichloromethane, 1:1) and addition of 4-benzyloxybenzoyl chloride and triethylamine gives the 4-benzyloxybenzamide of 3R-amino-6-nitro-2H-3,4-dihydro-[2-1b]imidazopyran.

EXAMPLE 24

N-Methyl, N-4-Benzyloxybenzyl 3R-Amino-6-nitro-2H-3,4-dihydro-[2-1b]imidazopyran

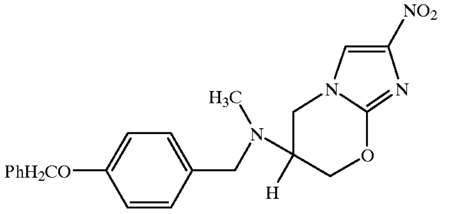

The N-Boc protected amine prepared in Example 23 is stirred with sodium hydride (1.1 eq.) and methyl iodide at 0° C. to room temperature. Following workup, the N-methyl amide is isolated. The Boc group is removed as described in Example 23 and the resulting methylamine is stirred with 4-benzyloxybenzaldehyde, sodium cyanoborohydride in methanol to give N-methyl, N-4-benzyloxybenzyl 3R-amino-6-nitro-2H-3,4-dihydro-[2-1b]imidazopyran.

EXAMPLE 25

Minium Inhibitory Concentrations (MIC) of 3(R) Substituted 6-Nitro-2H-3,4-dihydro-[2-1b] imidazopyran Antibacterial Compounds Against *M. bovis, M. tuberculosis* (Sensitive and Multi-drug Resistant) and *Clostridium difficile*

In Vitro Inhibition of *Clostridium difficile*

Minimum inhibitory concentration (MIC; $\mu$g/mL) of test drugs against *Clostridium difficile* ATCC 17857 was determined by broth microdilution method using inoculum, media, incubation conditions and end-point in accordance with approved standards of the National Committee for Clinical Laboratory Standards (NCCLS, National Committee for Clinical Laboratory Standards. 1993. *Methods for antimicrobial susceptibility testing of anaerobic bacteria.*

M11-A3. Third edition. National Committee: for Clinical Laboratory Standards, Villanova, Pa.) except for the following modification: Oxyrase® enzyme (Oxyrase Inc., Mansfield, Ohio) was incorporated in Wilkins-Chalgren broth (Remel, Lenexa, Kans.) to produce anaerobic conditions and preclude any requirement for anaerobic atmosphere incubation (Spangler, S. K. et al. "Oxyrase, a method which avoids $CO_2$ in the incubation atmosphere for anaerobic susceptibility testing of antibiotics affected by $CO_2$," *J. Clin. Microbiol.* 31:460–462 (1993); Spangler, S. K. et al., "Susceptibilities of 201 anaerobes to erythromycin, azithromycin, clarithromycin, and roxithromycin by Oxyrase agar dilution and E-test methodologies," *J. Clin. Microbiol.* 33:1366–1367 (1995)). Thus, the use of this method allowed incubation in ambient air rather than the $CO_2$, $H_2$ and $N_2$_ enriched atmosphere normally present in anaerobic chambers and jars. The Oxyrase both dilution method precluded the need of such equipment and provided a mechanism of avoiding the effects of $CO_2$ on the pH of the medium and in turn on the activity of test compounds. Falsely elevated MICs due to $CO_2$_ dependent decrease in the pH has been previously demonstrated (Barry, A. L. et al., "In-vitro potency of azithromycin against gram-negative bacilli is method-dependent," *J. Antimicrob. Chemother.,* 28:607–610 (1991), Hansen, S. L. et al., "Effect of carbon dioxide and pH on susceptibility of Bacteroides fragilis group to erythromycin," *Antimicrob. Agents Chemother.,* 19:335–336 (1981), Retsema, J. A. et al., "Significance of environmental factors on the in vitro potency of azithromycin," *Eur. J. Clin. Microbiol. Infect. Dis.,* 10:834–842 (1991)). This problem was eliminated by using Oxyrase, since this enzyme removed $O_2$ rapidly converting it to $H_2O$ without toxic intermediates. Quality control anaerobic microorganisms (*Bacteroides thetaiotamicrons* ATCC 29741; *Eubacterium lentum* ATCC 43055) were tested in Oxyrase broth microdilution against clindamycin, metronidazole, mezlocillin, and vancomycin for quality assurance. Results were accepted when MICs of these recommended strains were within the acceptable ranges published by the NCCLS National Committee for Clinical Laboratory Standards, *Methods for antimicrobial susceptibility testing of anaerobic bacteria*. M11-A3. Third edition. National Committee for Clinical Laboratory Standards, Villanova, Pa., 1993).

In Vitro Inhibition using (rBCG) LUX Method

Stock solutions of test compounds were prepared in dimethyl sulfoxide (DMSO; Sigma). These stocks were further diluted in DMSO to obtain concentrations suitable for minimum inhibitory concentration (MIC) or screening determinations. For MIC tests, two-fold dilutions ranging from 8.0 μg/mL to 0.002 μg/mL were used. For screening purposes, four concentrations were tested: 25.0, 5.0, 1.0 and 0.2 μg/mL.

A recombinant strain of *Mycobacterium bovis* bacille Calmette Guerin (rBCG) was employed as the challenge organism. This strain was transformed with an integrative shuttle vector carrying a firefly luciferase (lux) expression cassette. This vector was designated pMV361-lux.

A logarithmic phase culture of the rBCG:pMV361-lux strain was prepared in Middlebrook 7H9 broth (Difco) supplemented with 10% (v/v) ADC enrichment (BBL) and 0.5% (v/v) glycerol. The culture was diluted to obtain a final bacterial inoculum of $1\times10^5$ colony forming units per mL. A 2 mL culture volume was inoculated with 50 μL of each concentration of test compound. Control tubes containing rBCG:pMV361-lux in the absence of antibiotic were included. Isoniazid (Sigma) was included as a control in each assay run. Assay tubes were incubated at 37° C. for 6 days.

Luciferase activity was assessed by assay of 0.1 mL aliquots from each tube in an opaque white 96-well microtiter plate. Reactions were initiated by automated injection of 0.1 mL luciferin (1 mM) in a Wallac Autolumat model 96P luminometer. The MIC or lowest active concentration value was defined as the lowest concentration of compound which yielded a luminescence reading $\leqq 1/100$ the value obtained for the antibiotic-free growth control.

Minimum Inhibitory Concentration (MIC) as Determined by the BACTEC® Method

The BACTEC® system, available from Becton-Dickenson Diagnostic Instrument Systems. Sparks, Md., uses a radiorespirometric principle whereby carbon dioxide released by catabolism of $^{14}C$-labeled palmitic acid is spectrophotometrically detected and quantitated in arbitrary units of measurement referred to as Growth Index (GI) units. Endpoint determination criteria for BACTEC protocols are based on a conventional 1% resistance cut-off, wherein the organism under scrutiny is deemed resistant to the concentration of drug being tested if growth of greater than 1% of the bacterial population is observed. Thus, a comparison is made between growth in the presence of the antimicrobial agent and growth of the same organism diluted $10^{-2}$ in drug-free medium. BACTEC vials are inoculated with 0.1 mL of the organism (final bacterial concentration, $1-5\times10^5$ colony forming units per mL) and 0.1 mL of various concentrations of the antimicrobial agent. GI values are monitored daily until a value of $\geqq 30$ is achieved for the $10^{-2}$ control. The change in GI values (GI) is then used to determine susceptibility of the organism to each agent concentration tested. If the GI of the control is greater than that of the drug, then the organism is considered susceptible to that concentration. Conversely, if the GI of the control has a lower value than that of the drug, this indicates resistance. The drug is considered to have borderline activity at a particular concentration if the GI value of the control and drug are equal.

Minimum Inhibitory Concentrations (MICs)

The minimum inhibitory concentrations (MIC) of various 3(S) substituted 6-nitro-2H-3,4-dihydro-[2-1b] imidazopyran antibacterial compounds against *M. bovis* BCG (recombinant strain, using LUX method described above), *M. tuberculosis* (H37Rv sensitive strain and multidrug-resistant, both using the BACTEC method) and *Clostridium difficile* were determined for compounds synthesized using the procedures described herein having the general structure:

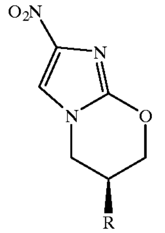

where R is the substituent shown in Table 1. The results are shown in Table 1.

TABLE 1

Minimum Inhibitory Concentrations (MIC) of 3(S) Substituted 6-Nitro-2H-3,4-dihydro-[2-1b]imidazopyran Antibacterial Compounds Against *M. bovis, M. tuberculosis* (Sensitive and Multidrug-Resistant) and *Clostridium difficile*

| PA | | MIC (μg/mL) | | | |
|---|---|---|---|---|---|
| No. | R | A[a] | B[b] | C[b] | D |
| 602 | —$OCH_2(CH_2)_6CH_3$ | <5.0 | — | — | 3.12 |
| 626 | —O-geranyl | 0.5 | 0.13 | — | 0.8 |
| 636 | —$OCH_2$4-$CF_3C_6H_4$ | 0.5 | — | — | 3.12 |
| 646 | —$OCH_2$2,4-di$CF_3C_6H_3$ | <5.0 | — | — | 3.12 |
| 647 | —$OCH_2$4-Bn$OC_6H_4$ | 0.03 | 0.03 | ≦0.015 | 12.50 |
| 651 | —$OCH_2C_6H_5$ | >5.0 | — | — | 3.12 |
| 652 | —$OCH_2C_6F_5$ | >5.0 | — | — | 3.12 |
| 653 | —$OCH_2$4-t-butyl$C_6H_4$ | 0.06 | 0.03 | ≦0.015 | 3.12 |
| 654 | —$OCH_2$2,4-di$FC_6H_3$ | >5.0 | — | — | 3.12 |
| 655 | —$OCH_2$4-$FC_6H_4$ | >5.0 | — | — | 6.25 |
| 736 | —$OCH_2$4-$CH_3OC_6H_4$ | 8.0 | — | — | — |
| 820 | —$OCH_2$3-Bn$OC_6H_4$ | <5.0 | — | — | 3.12 |
| 822 | —$OCH_2$4-n-butyl$C_6H_4$ | 0.06 | — | ≦0.015 | 12.5 |
| 824 | —$OCH_2$4-$CF_3OC_6H_4$ | 0.06 | — | 0.13 | — |
| 1122 | —$OCH_2$4-Ph$OC_6H_4$ | 0.06 | — | — | — |
| 1125 | —NHCO4-Bn$OC_6H_4$ | 0.06 | — | — | 1.5 |
| 1139 | —NHCOn-octyl | 0.06 | — | — | 3.12 |
| 1142 | —$OCH_2$4-n-octyl$C_6H_4$ | 0.06 | — | — | 1.5 |
| 1150 | —NHCO4-$CF_3OC_6H_4$ | 0.5 | — | — | — |
| 1170 | —NHCOC($OCH_3$)$CF_3C_6H_4$ | 0.13 | — | — | — |
| 1282 | —$NHCONH_4$-$ClC_6H_4$ | ≦0.002 | — | — | — |
| 1297 | —$OCONH_4$-$OCF_3C_6H_4$ | 0.015 | — | — | 0.78 |
| 1298 | —$NHCONH_4$-$CF_3OC_6H_4$ | 0.015 | — | — | — |
| 1324 | —$OCONH_4$-$BrC_6H_4$ | 0.015 | — | — | — |
| 1325 | —$NHCOCH_2C_6H_4$ | 0.06 | — | — | — |
| 1327 | —$OCONH_4$-$CF_3C_6H_4$ | 0.25 | — | — | — |
| 1328 | —$OCONHCH_2$4-$OCF_3C_6H_4$ | 0.03 | — | — | — |
| 1343 | —$NHCOOCH_2$4-$OCF_3C_6H_4$ | 0.015 | — | — | — |
| 1344 | —$NHCOOCH_2$4-$OCF_3C_6H_4$ | 0.008 | — | — | — |

[a]LUX method
[b]BACTEC method
A = *Mycobacterium bovis* BCG (recombinant strain), LUX method
B = *Mycobacterium tuberculosis* H37Rv (sensitive strain), BACTEC method
C = *Mycobacterium tuberculosis* (multidrug-resistant strain), BACTEC method
D = *Clostridium difficile* ATCC 17857
Bn = Benzyl
Ph = Phenyl

EXAMPLE 26

Minium Inhibitory Concentrations (MIC) of 3(R) Substituted 6-Nitro-2H-3,4-dihydro-[2-1b] imidazopyran Antibacterial Compounds Against *M. bovis, M. tuberculosis* (Sensitive and Multidrug-Resistant) and *Clostridium difficile*

The procedures of Example 25 were followed to determine the minimum inhibitory concentrations of various 3(R) substituted 6-nitro-2H-3,4-dihydro-[2-1b]imidazopyran antibacterial compounds prepared using the procedures described herein, having the following general formula:

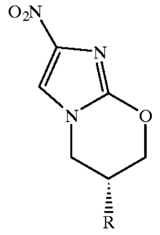

where R is the substituent shown in Table 1. The results are shown in Table 2.

TABLE 2

Minimum Inhibitory Concentrations (MIC) of 3(R) Substituted 6-Nitro-2H-3,4-dihydro-[2-1b]imidazopyran Antibacterial Compounds Against *M bovis, M. tuberculosis* (Sensitive and Multi-drug Resistant) and *Clostridium difficile*

| | | MIC (mg/ml) | | | |
|---|---|---|---|---|---|
| PA No. | R | A[a] | B | C[b] | D |
| 601 | —$OCH_2(CH_2)_6CH_3$ | 8.0 | — | — | 1.50 |
| 684 | —O-geranyl | >5.0 | — | — | 6.25 |
| 685 | —$OCH_2$4-$CF_3C_6H_4$ | >5.0 | — | — | 12.50 |
| 686 | —$OCH_2$2,4-di$CF_3C_6H_3$ | >5.0 | — | — | 3.12 |
| 687 | —$OCH_2$4-Ph$CH_2OC_6H_4$ | >5.0 | — | — | 6.25 |
| 692 | —$OCH_2C_6H_5$ | >5.0 | — | — | 6.25 |
| 693 | —$OCH_2C_6F_5$ | >5.0 | — | — | 6.25 |
| 694 | —$OCH_2$4-t-butyl$C_6H_4$ | >5.0 | — | — | 1.5 |
| 695 | —$OCH_2$2,4-di$FC_6H_3$ | >5.0 | — | — | 6.25 |
| 696 | —$OCH_2$4-$FC_6H_4$ | >5.0 | — | — | 6.25 |

[a]LUX method
[b]BACTEC method
A = *Mycobacterium bovis* BCG (recombinant strain), LUX method
B = *Mycobacterium tuberculosis* H37Rv (sensitive strain), BACTEC method
C = *Mycobacterium tuberculosis* (multidrug-resistant strain), BACTEC method
D = *Clostridium difficile* ATCC 17857

EXAMPLE 27

In Vivo Inhibition of Mycobacterium Species

Compounds were tested for in vivo activity against mycobacterial strains which had been transformed with vectors carrying the firefly luciferase gene (lux). Early experiments used a recombinant *Mycobacterium bovis* bacille Calmette Guerin (rBCG) strain, whereas later studies were performed with a recombinant *Mycobacterium tuberculosis* Erdman (rMTB) strain. The rBCG strain had been transformed with an extrachromosomal vector designated pMH30; the rMTB strain had been transformed with an integrative vector termed pHM46. Female BALB/c mice aged 4 to 6 weeks were used. Five animals were included in each test group. One group was included which did not receive any drug therapy. Logarithmic phase cultures of the mycobacterial strains were prepared in Middlebrook 7H9 broth (Difco) supplemented with 10% (v/v) ADC enrichment (BBL). 0.5% (v/v) glycerol and 20 μg/mL kanamycin.

A 150 μl volume of culture containing approximately $1\times10^7$ colony forming units per mL was injected into the tail vein of each mouse. Drug therapy was initiated 1 day or 7 days after infection with the rBCG or rMTB strains respectively. Test compounds were administered daily by oral gavage. For the rBCG experiments, test compounds were dissolved in DMSO/sesame oil and administered to mice at 50 mg/kg. For the *Mycobacterium tuberculosis* Erdman (rMTB) mouse protection studies, test compounds were delivered in the CM-2 formulation (see Example 52) at a dose of 25 mg/kg. Animals were sacrificed by cervical dislocation 10 days after initiation of therapy. Spleens and lungs were removed from each animal and homogenized in sterile Dulbecco's PBS (Gibco) containing 1% Triton X-100. Duplicate 200 μL aliquots of the homogenate were assayed in a Wallac Autolumat model 953B luminometer. Mean RLU values, standard deviation from the mean and statistical significance (paired, two-tailed t-test) were calculated. The results are shown in the following Tables 3a–3c:

TABLE 3a

In vivo Antimycobacterial Activity of 3(S) Substituted 6-Nitro-3,4-dihydro-[2-1b]imidazopyran Antibacterial Compounds Against *Mycobacterium bovis* (rBCG) in Spleens

| Compound | Average RLUs | Std. Deviation | p Value[A] |
|---|---|---|---|
| control[B] | 1,102,311 | 162,572 | — |
| PA-647 | 19,916 | 3,038 | 0.00012 |
| PA-653 | 229,080 | 77,685 | 0.00085 |

TABLE 3b

In vivo Antimycobacterial Activity of 3(S) Substituted 6-Nitro-3,4-dihydro-[2-1b]imidazopyran Antibacterial Compounds Against Mycobacterium tuberculosis (rMTB) in Spleens

| Compound | Average RLUs | Std. Deviation | p Value[A] |
|---|---|---|---|
| control[B] | 422,866 | 126,978 | — |
| PA-824 | 53,540 | 13,486 | 0.00295 |
| PA-636 | 91,377 | 18,604 | 0.00435 |
| PA-1297 | 66,473 | 20,494 | 0.00221 |
| control | 362,274 | 61,353 | — |
| PA-1324 | 85,130 | 9,157 | 0.00066 |
| PA-1325 | 213,675 | 25,517 | 0.00211 |
| PA-1327 | 68,362 | 4,705 | 0.00038 |
| PA-1328 | 251,264 | 198,257 | 0.377 |
| PA-1343 | 51,928 | 10,166 | 0.00043 |

TABLE 3c

In vivo Antimycobacterial Activity of 3(S) Substituted 6-Nitro-3,4-dihydro-[2-1b]imidazopyran Antibacterial Compounds Against Mycobacterium tuberculosis (rMTB) in Lungs

| Compound | Average RLUs | Std. Deviation | p Value[A] |
|---|---|---|---|
| control[B] | 117,258 | 64,777 | — |
| PA-824 | 2,496 | 1,539 | 0.0159 |
| PA-636 | 5,790 | 1,857 | 0.0191 |
| PA-1297 | 3,354 | 1,143 | 0.0174 |
| control | 22,751 | 9,152 | — |
| PA-1324 | 1,612 | 614 | 0.00587 |
| PA-1325 | 17,606 | 8,289 | 0.528 |
| PA-1327 | 1,561 | 636 | 0.00709 |
| PA-1328 | 3,000 | 995 | 0.00985 |
| PA-1343 | 606 | 277 | 0.00582 |

[A]Statistical significance from paired, two-tailed t-test
[B]Infected but not treated animals which served as the negative control

EXAMPLE 28

3S-Azido-6-nitro-2,3-dihydro-[2-1b]imidazopyran

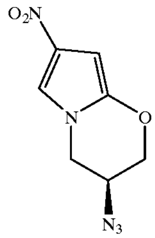

Method A

3R-Hydroxy-6-nitro-2H-3,4-dihydro-[2-1b] imidazopyran p-Toluenesulfonate

A solution of 1 g (5.4 mmol) of the alcohol prepared in Example 7 in dry pyridine (5 mL), and 2 g (10.5 mmol) of p-toluenesulfonyl chloride was stirred at 40–50° C. overnight. The reaction mixture was poured into cold water and the precipitant was collected by filtration, washed with methanol, and dried ($MgSO_4$) to give 1.54 g (83%) of the title compound: $^1H$ NMR (DMSO): δ 2.44 (s, 3H), 4.20 (d, 1H), 4.32–4.45 (m, 2H), 4.57 (d, 1H), 7.51 (d, 2H), 7.87 (d, 2H), 8.81 (s, 1H); $^{13}C$ NMR (DMSO) δ 22.60, 48.65, 69.72, 71.07, 119.25, 129.08, 131.84, 133.86, 147.08; MS 340 $(M+H)^+$.

A solution of 430 mg (1.27 mmol) of the tosylate prepared above and 100 mg (1.53 mmol) of sodium azide in 5 mL dry DMSO was heated in an oil bath (65° C.) for 24 h. The reaction was cooled to room temperature, quenched with water and extracted with EtOAc. The organic extracts were dried ($MgSO_4$) and the solvent evaporated. The residue was recrystallized from ethyl acetate/hexane to give the azide as light yellow needles: mp 157.5° C. (dec.); $[\alpha]^{25}D$ (DMF, c=1.0)=−84.2°; $^1H$ NMR (DMSO) δ 4.18 (d, 1H), 4.33 (dd, 1H), 4.57 (d, 2H), 4.65 (d, 1H), 8.08 (s, 1H); $^{13}C$ NMR (DMSO) δ 48.11, 52.28, 69.57, 69.71, 119.39, 129.07, 131.82, 143.59, 148.14; MS 211$(M+H)^+$.

Method B (3R) 1-(2'-Hydoxy-3'-t-butyldimethylsilyloxy)-propyl-2,4-dinitroimidazole p-Toluenesulfonate The crude alcohol (12.4 g) obtained from Example 5 was dissolved in 50 mL dry pyridine and 14 g (73.5 mmol) of p-toluenesulfonyl chloride was added. The reaction was stirred at 60° C. for 6 h. Pyridine was removed by evaporation at reduced pressure and the residue was distributed between 300 mL of ethyl acetate and 300 mL of 0.01 N HCl aq. The organic layer was separated, dried over $MgSO_4$, and concentrated. The crude product was purified by recrystallization from ethyl acetate/hexane to give 8.1 g of the tosylate. A second crop of tosylate was obtained from the mother liquor by column chromatography (hexane:ethyl acetate, 6:1): yield 2.9 g. A total yield of 61% (11 g) was obtained: mp 139–141.5° C.; $^1H$ NMR ($CDCl_3$) δ 0.05 (s, 6H), 0.85 (s, 9H), 3.84 (dd, 1H), 3.93 (dd, 1H), 4.39 (dd, 1H), 4.77 (m, 1H), 4.90 (dd, 1H), 7.18 (d, 2H), 7.47 (d, 2H), 7.65 (s, 1H); $^{13}C$ NMR ($CDCl_3$) δ 4.55, 4.52, 19.21, 22.58, 26.74, 52.89, 63.97, 79.26, 125.57, 128.10, 131.16, 132.97, 144.06, 147.50; MS 443 (M- t-butyl)$^+$.

3R-Hydroxy-6-nitro-2H-3,4-dihydro-[2-1b] imidazolpyran p-Toluenesulfonate

The tosylate prepared above (9.4 g, 18.8 mmol) was dissolved in 60 mL of dry THF and 19 mL (1.0 M)

tetrabutylammonium fluoride in THF was added to the reaction mixture at room temperature. The resulting solution was stirred for 5 min at which time the product precipitated. The precipitate was washed with methanol and dried over $P_2O_5$ to give 4.66 g (73%) the tosylate identical to the sample prepared in Example 28.

EXAMPLE 29

3S-Amino-6-nitro-3,4-dihydro-[2-1b]imidazopyran

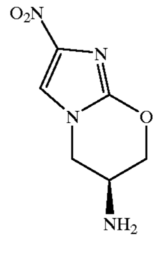

To a solution of the azido compound prepared in Example 28 (105 mg, 0.5 mmol) in 2.5 mL of freshly distilled dry methanol (magnesium metal) was added a 5-fold excess of propane-1,3-dithiol (0.25 mL) and triethylamine (0.348 mL). The reaction mixture was stirred at room temperature for 5 min during which time the reaction solution turned clear. Solvents were removed by reduced pressure evaporation and the residue was applied to a Dowex 50 ($H^+$ form in methanol) column and washed with methanol to remove the remained thiol. The product was obtained by eluting the column with methanol:triethylamine (19:1). After the removal of the sol-vents, the residue was neutralized with 0.5 mL of 1N HCl to pH 6 and the solution was evaporated to dryness giving 110 mg the title compound (100%): $^1H$ NMR (DMSO) δ 4.05 (s, 1H), 4.24 (d, 1H), 4.41 (dd, 1H), 4.61 (s, 2H), 8.18 (s, 1H); $^{13}C$ NMR (DMSO) δ 43.00, 49.85, 72.10, 119.56, 143.39, 148.74; MS 184 (amine M)$^+$.

EXAMPLE 30

4-Trifluoromethoxyphenylacetamide of 3S-(4-Amino)-6-nitro-3,4-dihydro-[2-1b]imidazopyran

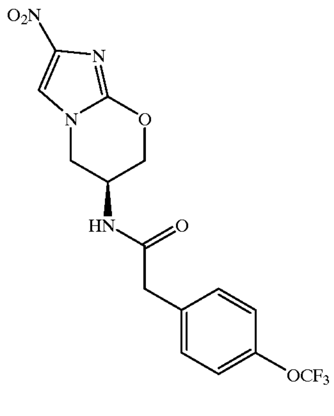

4-Trifluoromethoxybenzylcyanide

To a solution containing 2.085 g (8.18 mmol) of 4-trifluoromethoxybenzyl bromide in 10 mL dry DMF was added 441 mg (8.99 mmol) of sodium cyanide. The reaction was stirred for 1 h at room temperature, poured into water and extracted with of ethyl acetate (2x40 mL). The combined organic extracts were dried ($MgSO_4$) and evaporated. The crude product was used in the next reaction without further purification.

4-Trifluoromethoxyphenyl acetic acid

The cyanide obtained from above reaction was heated at reflux temperature in 50 mL 1N NaOH aq for 1 h and cooled to room temperature, and acidified to pH 3 with 1N $H_2SO_4$. A white solid was collected and dried over $P_2O_5$ affording 1.6 g of acid (total yield for two steps 88.9%): mp 85–86° C.; $^1H$ NMR (DMSO) δ 3.66 (s, 2H), 7.30 (d, 2H), 7.41 (d, 2H), 12.50 (broad, 1H); 13C NMR (DMSO) δ 122.09, 132.64, 135.96, 148.63, 173.74.

A solution of 4-Trifluoromethoxyphenyl acetic acid (110 mg, 0.5 mmol), 110 mg (0.5 mmol), of the amine hydrochloride salt prepared in Example 29, 227 mg (0.6 mmol) of HBTU, and 121 mg of (1.2 mmol) N-methylmorpholine (NMM) in 5 mL of DMF was stirred at room temperature for 4 h. The product was extracted with ethyl acetate, washed with 0.01 N HCl, sat. $NaHCO_3$, and water. The organic layer was separated, dried ($MgSO_4$), and concentrated under reduced pressure. The residue was purified on a silica gel column using ethyl acetate as the eluant affording 136 mg (70%) of the title compound: mp 167–168° C. (dec.); $^1H$ NMR ($CDCl_3$) δ 4.16–4.53 (m, 5H), 5.11 (s, 2H), 7.13–7.34 (m, 6H); $^{13}C$ NMR ($CDCl_3$) δ 43.61, 48.96, 67.04, 70.58, 116.40, 121.91, 130.17, 144.13, 148.30; MS 403 $(M+H)^+$.

EXAMPLE 31

Phenylacetamide of 3S-Amino-6-nitro-3,4-dihydro-[2-1b]imidazopyran

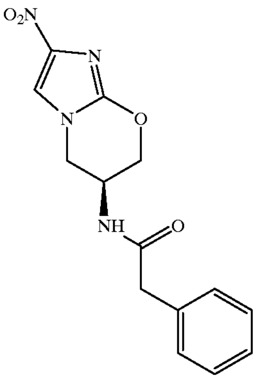

Using the procedure described in Example 30 and substituting phenyl acetic acid for 4-trifluoromethoxyphenyl acetic acid gave the title compound: mp 182.5° C. (dec.); $^1H$ NMR ($CDCl_3$) δ 3.64 (s, 2H), 4.00 (d, 1H), 4.16 (dd, 1H), 4.33 (dd, 1H), 4.50 (d, 1H), 4.77 (m, 1H), 7.20–7.31 (m, 6H), 8.87 (d, 1H); $^{13}C$ NMR ($CDCl_3$) d 41.27, 43.83, 49.02, 71.03, 116.09, 127.84, 129.46, 130.32, 136.27, 143.94, 148.76, 172.84; MS 303 $(M+H)^+$.

EXAMPLE 32

4-Trifluoromethoxybenzyl Carbamate of 3S 3-Hydroxy-6-nitro-3,4-dihydro-[2-1b]imidazopyran

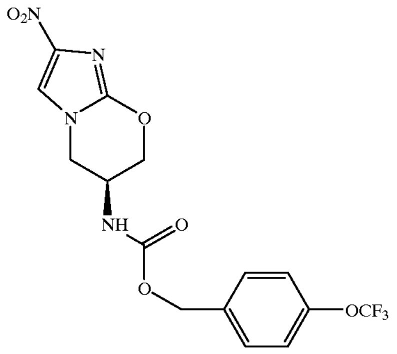

A flask containing 0.39 mL (0.75 mmol) of phosgene (1.93 M in toluene) and 96 mg (0.5 mmol) of trifluoromethoxybenzyl alcohol was cooled in an ice-bath and 65 μL (0.5 mmol) of diisopropylethylamine was added. After the reaction was stirred for 30 min, excess phosgene was removed under reduced pressure. The crude chloroformate was disolved in 2 mL of dichloromethane and 110 mg (0.5 mmol) of the amine salt prepared in Example 29 and 129 μL of diisopropylethyl amine was added. The reaction mixture was stirred for 1 h at room temperature and the solvents removed. The crude carbamate was purified by silica gel chromatography (hexane:ethyl acetate 1:3) to obtain the title compound (referred to in Example 25 as PA No. 1343). Yield: 117 mg (58%); mp 132.5–133.5° C.; $^{1}H$ NMR ($CDCl_3$) δ 4.16–4.53 (m, 5H), 5.11 (s, 2H), 7.31–7.34 (m, 6H); $^{13}C$ NMR ($CDCl_3$) d 43.61, 48.96, 67.04, 70.58, 116.40, 121.91, 130.17, 144.13, 148.30; MS 403 $(M+H)^+$.

EXAMPLE 33

4-Bromophenyl Carbamate of 3S Hyrdroxy-6-nitro-2H-3,4-dihydo-[2-1b]imidazopyran

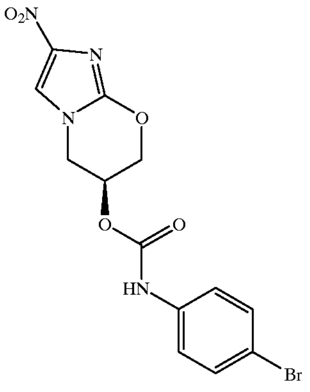

To a solution of 210 mg (1.13 mmol) of the alcohol prepared in Example 3 and 246 mg (1.24 mmol) of 4-bromophenyl isocyanate in dry DMF (5 mL) was added copper chloride (0.11 mmol). The reaction mixture was stirred at room temperature for 3 h, cooled to room temperature, and EtOAc (50 mL) was added. The organic solution was washed with 0.2 M HCl (20 mL), and water (2×40 mL). The organic extracts were separated, dried ($MgSO_4$), and the solvent evaporated. The residue was purified by column chromatography (hexane:EtOAc) to give 334 mg (77%) of the title compound: mp 235° C. (dec.); $^{1}H$ NMR (DMSO) δ 10.06 (s, 1H), 8.09 (s, 1H), 7.46 (m, 4H), 5.43 (s, 1H), 4.65 (s, 2H), 4.41 (q, 2H); MS 383 $(M+H)^+$.

Anal. calcd. for $C_{13}H_{11}N_4O_5Br$: C, 40.75; H, 2.89; N, 14.62. Found: C, 40.77; H, 2.92; N, 14.51.

EXAMPLE 34

4-(Trifluoromethoxy)phenyl Carbamate of 3S Hydroxy-6-nitro-2H-3,4-dihydo-[2-1b]imidazopyran

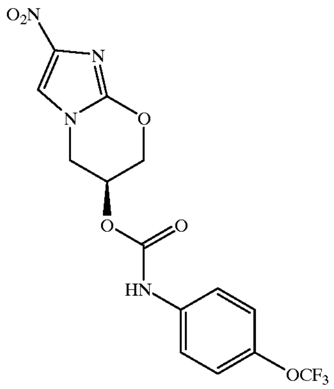

Using the procedure described in Example 33 and substituting 4-(trifluoromethoxy)phenyl isocyanate for 4-bromophenyl isocyanate gave the title compound: mp 220° C. (dec.); $^{1}H$ NMR (DMSO) δ 10.12 (s, 1H), 8.09 (s, 1H), 7.55 (d, 2H) 7.32 (d, 2H), 5.44 (s, 1H), 4.61 (s, 2H), 4.35 (q, 2H); MS 388 $(M+H)^+$.

Anal. calcd. for $C_{14}H_{11}N_4O_6F_3$: C, 43.31; H, 2.86; N, 14.43. Found: C, 43.23; H, 2.87; N, 14.32.

EXAMPLE 35

4-(Trifluoromethyl)phenyl Carbamate of 3S Hydroxy-6-nitro-2H-3,4-dihydo-[2-1b]imidazopyran

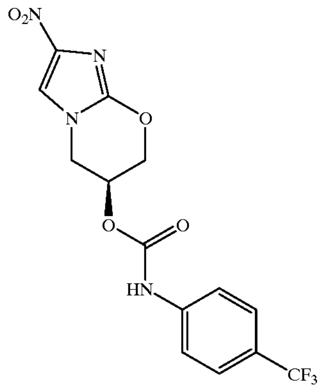

Using the procedure described in Example 33 and substituting 4-(trifluoromethyl)phenyl isocyanate for 4-bromophenyl isocyanate gave the title compound (referred to in Example 25 as PA No. 1327): mp 240° C. (dec.); $^{1}H$ NMR (DMSO) δ 10.33 (s, 1H), 8.10 (s, 1H), 7.67 (s, 4H), 5.47 (s, 1H), 4.66 (s, 2H), 4.38 (q, 2H); MS 373 $(M+H)^+$.

Anal. calcd. for $C_{14}H_{11}N_4O_5F_3$: C, 45.17; H, 2.98; N, 15.05. Found: C, 44.60; H, 2.89; N, 14.86.

EXAMPLE 36

4-(Trifluoromethoxy)benzyl Carbamate of 3S Hydroxy-6-nitro-2H-3,4-dihydo-[2-1b]imidazopyran

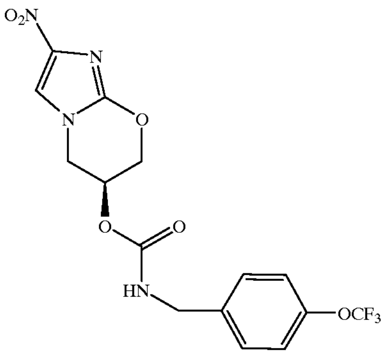

To a solution of 207 mg (1.12 mmol) of the alcohol prepared in Example 3 and 217 mg (1.34 mmol) of 1,1-carbonyldiimidazole in dry DMF (5 mL) at −60° C., was added sodium hydride (1.34 mmol) in portions. The reaction mixture was allowed to stir at room temperature for 3 h. 4-(Trifluoromethoxy)benzyl amine was added and the reaction was stirred at room temperature for 1 h, diluted with EtOAc (50 mL), quenched with 0.2 M HCl (40 mL), the organic layer separated, washed with water (2×40 mL), dried ($MgSO_4$), and the solvent evaporated. The residue was subjected to column chromatography (EtOAc:hexane) affording 82 mg (18%) of the title compound: mp 182° C. (dec.); $^1H$ NMR (DMSO) δ 8.09 (d, 2H), 7.35 (d, 4H), 5.30 (s, 1H), 4.57 (s, 2H), 4.21–4.35 (m, 4H); MS 403 $(M+H)^+$.

Anal. calcd. for $C_{15}H_{13}N_4O_6F_3$: C, 44.79; H, 3.26; N, 13.93. Found: C, 44.61; H, 3.26; N, 13.82.

EXAMPLE 37

3S 4-(Trifluromethyl)benzyloxy-6-nitro-2H-3,4-dihydo-[2-1b]imidazopyran

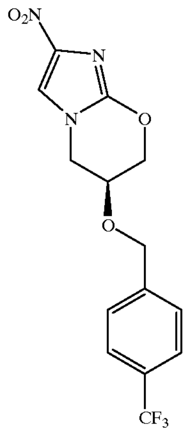

Using the procedure described in Example 41 and substituting 4-trifluoromethylbenzyl chloride for 4-(trifluoromethoxy)benzyl bromide gave the title compound (referred to in Example 25 as PA No. 636) in 68% yield: mp 215–216° C.; $^1H$ NMR (DMSO) δ 8.04 (s, 1H), 7.70 (d, 2H), 7.54 (d, 2H), 4.76 (m, 3H), 4.50 (d, 1H), 4.27 (m, 3H); MS 344 $(M+H)^+$.

Anal. calcd. for $C_{14}H_{12}N_3O_4F_3$: C, 48.99; H, 3.52; N, 12.24. Found: C, 48.45; H, 3.53; N, 12.11.

EXAMPLE 38

4-(2,2,2-Trifluoroethoxy)phenyl Carbamate of 3S Hydroxy-6-nitro-2H-3,4-dihydo-[2-1b]imidazopyran

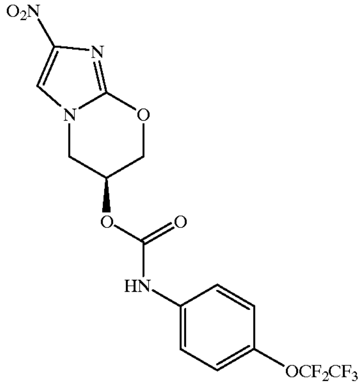

Using the procedure described in Example 36 and substituting 4-(2,2,2-trifluoroethoxy)aniline (*Chem. Pharm. Bull.,* 44(2):314–327 (1996)) for 4-(trifluoromethoxy) benzyl amine gives the title compound.

EXAMPLE 39

4-(2,2,3,3-Tetrafluoropropoxy)phenyl Carbamate of 3S Hydroxy-6-nitro-2H-3,4-dihydo-[2-1b] imidazopyran

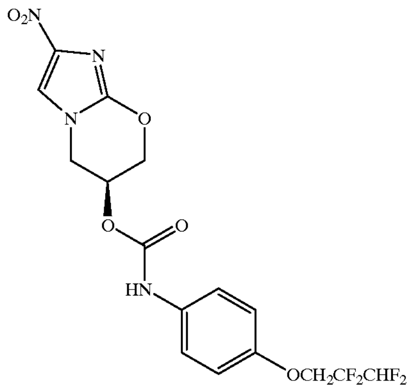

Using the procedure described in Example 36 and substituting 4-(2,2,3,3-tetrafluoropropoxy)aniline (*Chem. Pharm. Bull.,* 44(2):314–327 (1996)) for 4-(trifluoromethoxy)benzyl amine gives the title compound.

EXAMPLE 40

4-(2,2,3,3,3-Pentafluoropropoxy)phenyl Carbamate of 3S Hydroxy-6-nitro-2H-3,4-dihydo-[2-1b] imidazopyran

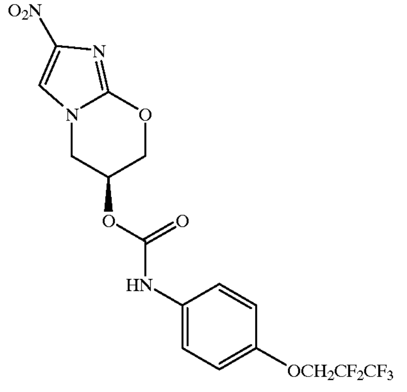

Using the procedure described in Example 36 and substituting 4-(2,2,3,3,3-pentafluoropropoxy)aniline (*Chem. Pharm. Bull.*, 44(2):314–327 (1996)) for 4-(trifluoromethoxy)benzyl amine gives the title compound.

EXAMPLE 41

3S 4-(Trifluromethoxy)benzyloxy-6-nitro-2H-3,4-dihydro-[2-1b]imidazopyran

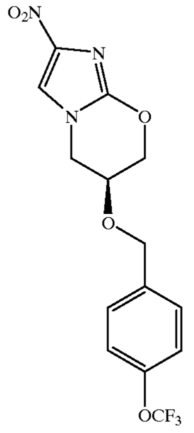

To a solution of 4-(trifluoromethoxy)benzyl bromide (0.09 mol) and the alcohol (0.075 mol) which was prepared in Example 3 in dry DMF (90 mL) cooled to −60° C. was added sodium hydride (0.09 mol) over 5 min. After 1 h the reaction mixture was warmed to room temperature and stirred for 2 additional hours. The reaction mixture was diluted with EtOAc (400 mL), washed with water (3×200 mL), dried ($MgSO_4$), and the solvent evaporated. The residue was subjected to column chromatography (EtOAc:hexane) and the product obtained was recrystallized from boiling methanol, yielding 18.6 g (70%) of the title compound (referred to in Example 25 as PA No. 824): mp 149–150° C.; $^1$H NMR (DMSO) δ 8.05 (s, 1H), 7.43 (d, 2H), 7.35 (d, 2H), 4.69 (m, 3H), 4.50 (d, 1H), 4.26 (m, 3H); MS 360 $(M+H)^+$.

Anal. cald. for $C_{14}H_{12}N_3O_5F_3$: C,46.81; H,3.37; N, 11.70. Found: C, 46.58; H, 3.34; N, 11.67.

EXAMPLE 42

3S 4-(Iodo)benzyloxy-6-nitro-2H-3,4-dihydo-[2-1b] imidazopyran

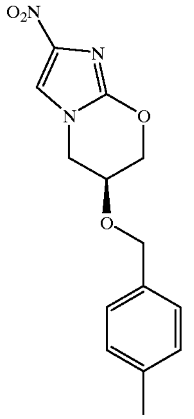

Using the procedure described in Example 41 and substituting 4-iodobenzyl bromide (prepared in two steps from 4-iodobenzoic acid by reduction of the acid with borane in THF followed by bromination of the benzyl alcohol with $PBr_3$ in THF at 0° C.) for 4-(trifluoromethoxy)benzyl bromide gives the title compound.

EXAMPLE 43

3S 4-(trifluoroethoxy)benzyloxy-6-nitro-2H-3,4-dihydo-[2-1b]imidazopyran

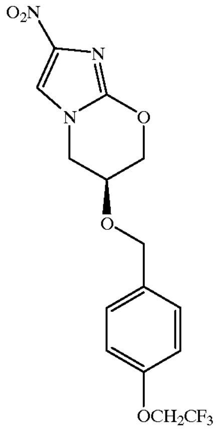

Using the procedure described in Example 41 and substituting 4-(trifluoroethoxy)benzyl bromide (prepared from ethyl 4-(trifluoroethoxy)benzoate (*Chem. Pharm. Bull.*, 44(2):314–327 (1996)) by lithium aluminum hydride reduction and bromination of the resulting benzyl alcohol with $PBr_3$) for 4-(trifluoromethoxy)benzyl bromide gives the title compound.

EXAMPLE 44

3S 4-(2,2,3,3-Tetrafluoropropoxy)benzyloxy-6-nitro-2H-3,4-dihydo-[2-1b]imidazopyran

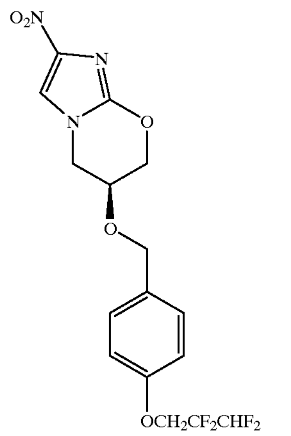

Using the procedure described in Example 41 and substituting 4-(2,2,3,3-tetrafluoropropoxy)benzyl bromide (prepared from ethyl 4-(2,2,3,3-tetrafluoropropoxy) benzoate (*Chem. Pharm. Bull.,* 44(2):314–327 (1996)), lithium aluminum hydride reduction and bromination of the resulting benzyl alcohol with $PBr_3$) for 4-(trifluoromethoxy) benzyl bromide gives the title compound.

EXAMPLE 45

3S 4-(2,2,3,3,3-Pentafluoropropoxy)benzyloxy-6-nitro-2H-3,4-dihydo-[2-1b]imidazopyran

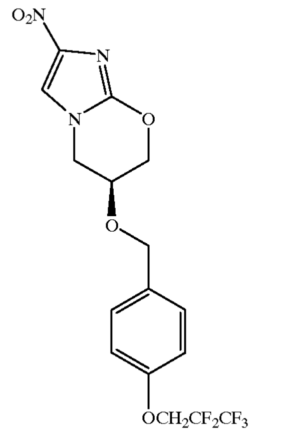

Using the procedure described in Example 41 and substituting 4-(2,2,3,3,3-pentafluoropropoxy)benzyl bromide (prepared from ethyl 4-(2,2,3,3,3-pentafluoropropoxy) benzoate (*Chem. Pharm. Bull.,* 44(2):314–327 (1996)), lithium aluminum hydride reduction and bromination of the resulting benzyl alcohol with $PBr_3$) for 4-(trifluoromethoxy) benzyl bromide gives the title compound.

EXAMPLE 46

4-Chlorobenzyl Carbamate of 3S 3-Amino-6-nitro-3,4-dihydro-[2-1b]imidazopyran

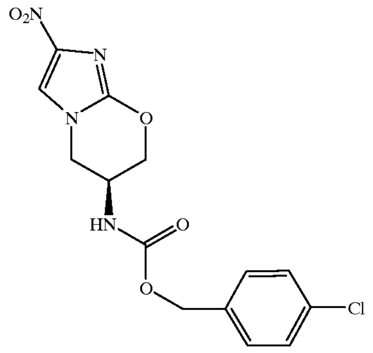

Using the procedure described in Example 32 and substituting 4-chlorobenzyl alcohol for 4-trifluoromethoxy benzyl alcohol gives the title compound.

EXAMPLE 47

4-Bromobenzyl Carbamate of 3S 3-Hydroxy-6-nitro-3,4-dihydro-[2-1b]imidazopyran

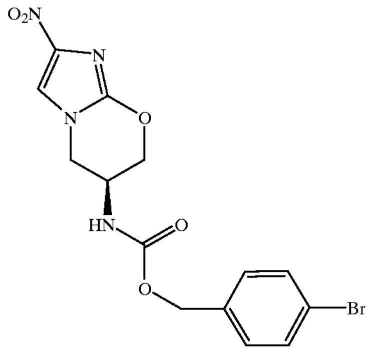

Using the procedure described in Example 32 and substituting 4-bromobenzyl alcohol for 4-trifluoromethoxy benzyl alcohol gives the title compound (referred to in Example 25 as PA No. 1324).

EXAMPLE 48

4-Chlorophenyl Urea of 3S 3-Amino-6-nitro-3,4-dihydro-[2-1b]imidazopyran

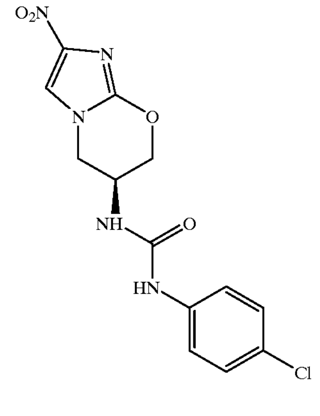

To a flask containing the amine hydrochloric acid salt 69 mg (0.312 mmol) prepared in Example 29 and N-methylmorpholine 63 mg (0.624 mmol) in DMF, was added 95 mg of 4-chlorobenzyl isocyanate in DMF. The reaction was stirred at room temperature for 1 h, poured into 0.01 N HCl and extracted with ethyl acetate. The organic extract was washed with saturated aq. $NaCO_3$, water, dried ($MgSO_4$) and evaporated. The residue was purified on a silica gel column using ethyl acetate as the eluant to give 93 mg (88%) of the title compound (referred to in Example 25 as PA No. 1282): $^1H$ NMR (DMSO) δ 4.074.58 (m, 5H), 6.92 (d, 1H), 7.28 (d, 2H), 7.40 (d, 2H), 8.10 (s, 1H), 8.56 (s, 1H); MS 338 $(M+H)^+$.

EXAMPLE 49

2-(5-Chlorobenzimidazole) Derivative of 3S 3-Amino-6-nitro-3,4-dihydro-[2-1b]imidazopyran

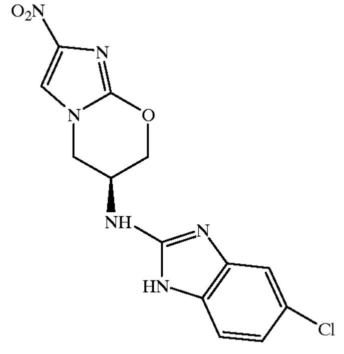

The title compound is prepared by reacting the amino compound prepared in Example 29 with 2,5-dichlorobenzimidazole using the procedures described in Great Britain Patent No. 1015937.

EXAMPLE 50

Inhibition of *Mycobacterium bovis* (rBCG) Under Anaerobic Conditions

A recombinant strain of *Mycobacterium bovis* bacille Calmette Guerin (rBCG) was employed as the test organism. This strain was transformed with an integrating shuttle vector carrying a firefly luciferase (lux) expression cassette, designated 361-lux. A logarithmic phase culture of rBCG:361-lux was prepared in Middlebrook 7H9 broth (Difco) supplemented with 10% (v/v) ADC enrichment (BBL). 2 ml aliquots were placed in 15 ml screw-cap plastic tubes, and oxygen was removed by addition of 40 μl Oxyrase For Broth (Oxyrase, Inc., Mansfield, Ohio). After 24 h incubation at 37° C., the compounds listed in Table 4 were added to final concentrations of 0, 0.15, 0.31, 0.62, 1.25, 2.5, or 5.0 μg/ml. Following 72 h anaerobic incubation with the drugs at 37° C., bacilli were vortexed on high for 10 sec, pelleted by centrifugation (10 min at 2500 RPM in a Beckman GS-6R centrifuge), and resuspended in fresh media as above. This procedure removed the drugs while recreating the aerobic environment. Since mycobacteria will not grow without oxygen even in the absence of inhibitory compounds, the effect of drugs under anaerobic conditions can only be measured after a suitable recovery period. Accordingly, reaerated, drug-free bacilli were incubated 48 h at 37° C., whereupon duplicate 100 μL aliquots of culture were assayed in a Wallac Microlumat LB 96P luminometer. Results are shown in Table 4.

TABLE 4

Anaerobic Activity of PA-824 and Other Anti-Mycobacterial Compounds Against *Mycobacterium bovis* (rBCG-lux)

| Drug conc. (μg/ml) | PA-824 | Streptomycin | Ethambutol | Amikacin | INH |
|---|---|---|---|---|---|
| 0 | 100 | 100 | 100 | 100 | 100 |
| 0.15 | 29.4 | 63.5 | 178.9 | 52.9 | 157.7 |
| 0.31 | 12.3 | 39.8 | 152.4 | 31.7 | 121.5 |
| 0.62 | 0.6 | 19.6 | 98.8 | 18.9 | 110.0 |
| 1.25 | 0.3 | 11.7 | 148.3 | 18.1 | 51.1 |
| 2.5 | 0.2 | 8.0 | 54.8 | 10.7 | 34.1 |
| 5.0 | 0.1 | 4.4 | 53.1 | 5.2 | 11.4 |

All values are % of control, measured in RLUs.

EXAMPLE 51

In Vitro Inhibition of *Helicobacter pylori*

Reference strains of *Helicobacter pylori* were obtained from Dr. Mike Osato, Department of Gastroenterology, Baylor College of Medicine, Huston, Tex. Minimum inhibitory concentrations (MIC, μg/mL) of the test drugs were determined by broth microdilution method using procedures in accordance with approved standards of the National Committee for Clinical Laboratory Standards and references cited therin (Coudron, P. E. and C. W. Stratton, *J. Clin. Microbiol* 33(4):1028–1030 (1995); DeCross, A. J., B. J. Marshall, R. W. McCallum, S. R. Hoffman, L. J. Barrett, and R. L. Guerrant, *J. Clin. Microbiol* 31(8):1971–1974 (1993); Malanoski, G. J., G. M. Eliopoulous, M. J. Ferraro, R. C. Moellering, *Eur. J. Clin. Microbiol. Infect. Dis.* 12(2):131–133 (1993), and National Committee for Clinical Laboratory Standards, *Methods for antimicrobial susceptibility testing of anaerobic bacteria*. M11-A3, Third edition, National Committee for Clinical Laboratory Standards, Villanova, Pa. (1993)), except for the following modifications:

1. Media: Brain heart infusion supplemented with 10% Equine serum, and 0.25% yeast extract
2. Incubation atmosphere: 35° C., 10% $CO_2$
3. Inoculum: 1:20 dilution of a suspension adjusted to 1 McFarland turbidity
4. Incubation time: 72 hours Test plates were examined visually at the end of the incubation and MIC values were determined as the lowest concentration which resulted in complete inhibition of growth.

Amoxicillin, Metronidazole, and Clarithromycin were tested against *H. pylori* ATCC 43 using the conditions described above. The resulting MICs were within the expected values for these drugs. The minimum inhibitory concentrations (MIC) of various 3(S)-substituted-6-nitro-2H-3,4-dihydro-[2-1b]imidazopyran antibacterial compounds against *H. pylori* ATCC 43 were determined for compounds synthesized using the procedures described herein having the general structure:

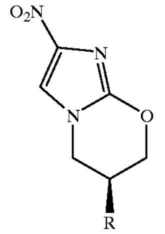

where R is the substituent shown in Table 1. The results are shown in Table 5A.

TABLE 5A

Minimum Inhibitory Concentrations (MIC) of 3(S) Substituted 6-Nitro-2H-3,4-dihydro-[2-1b]imidazopyran Antibacterial Compounds Against *Helicobacter pylori*

| Strain | MIC (μg/ml) | | | | | | | | |
|---|---|---|---|---|---|---|---|---|---|
| | PA No. | | | | | | | | |
| No. | 647 | 822 | 824 | 1125 | 1139 | 1142 | Cla | Amo | Met |
| 19 | 0.2 | 0.2 | 0.4 | 0.8 | 1.5 | 0.4 | 8 | 0.016 | 0.25 |
| 20 | 0.2 | 0.2 | 0.2 | 0.8 | 0.8 | 0.8 | 8 | 0.032 | 1 |
| 40 | 0.4 | 0.2 | 0.4 | 1.5 | 0.8 | 1.5 | 0.016 | 0.032 | 0.25 |
| 43 | 0.4 | 0.4 | 0.8 | 1.5 | 1.5 | 0.4 | 0.008 | 0.016 | 0.032 |
| 17 | >25 | 25 | >25 | >25 | >25 | >25 | 0.016 | 0.016 | 32 |
| 76 | 3.12 | 6.25 | 12.5 | >25 | 25 | 3.12 | 0.032 | 0.032 | 32 |
| ATCC 43504 | >25 | >25 | >25 | >25 | >25 | >25 | 0.06 | 0.06 | 128 |

[1]Clarithromycin
[2]Amoxycillin
[3]Metronidazole

The foregoing procedure was used to determine the MIC of the imidazopyran antibacterial compound PA1343 (see Table 1) against a panel *H. pylori* strains as indicated in Table 5B. The strains are characterized in the Table as being Metronidazole sensitive (Met-S), Metronidazole resistant (Met-R), Clarithromycin sensitive (Clar-S) and/or Clarithromycin resistant (Clar-R).

TABLE 5B

Minimum Inhibitory Concentrations (MIC) of the 3(S) Substituted 6-Nitro-2H-3,4-dihydro-[2-1b]imidazopyran Antibacterial Compound PA 1343 Against *Helicobacter pylori*

| | | MIC (μg/ml) | | |
|---|---|---|---|---|
| Strain No. | Characterization | PA No.1343 | Met[1] | Cla[2] |
| ATCC 43504 | Met-R, Clar-S | 10 | 128–256 | 0.03 |
| ATCC 43526 | Met-R, Clar-S | 12 | 16 | <0.015 |
| ATCC 43579 | Met-S, Clar-S | 1.5 | 2 | <0.015 |
| ATCC 43629 | Met-S, Clar-S | 3 | <0.5 | 0.03 |
| B40 | Met-S, Clar-S | 0.8 | <0.5 | <0.015 |
| B76 | Met-R, Clar-S | 12 | 8 | <0.015 |
| C11403 | Met-S, Clar-R | 1.5 | <0.5 | 4 |
| C1649 | Met-R, Clar-R | 12 | 16 | >4 |
| C19765 | | 12 | 8 | <0.015 |
| rd26 | Met-S, Clar-S | 2 | 1 | 0.03 |
| RD26 | Met-S, Clar-S | 3 | 1 | 0.03 |

[1]Metronidazole
[2]Clarithromycin

EXAMPLE 52

CM-2 Formulation for Oral and Intraveneous Administeration

PA 824 (Example 41, 10 mg) was added to a 1 mL solution of 10% (w/v) aqueous hydroxypropyl-β-cyclodextrin (Aldrich) and stirred for 24 h at room temperature. The resulting suspension was sonicated with a Vibra Cell sonicator (Sonics and Materials Inc.) for 10 min using a probe tip setting of 25% amplitude. Frozen lecithin (100 mg, 10% (w/v), Sigma) was added and the suspension was stirred for 10 min at room temperature, cooled in an ice-water bath, and sonicated at 30% amplitude for 15 min keeping the solution temperature less than 50° C. This formulation, with PA 824 or other compounds of the invention, is referred to herein as the CM-2 formulation.

EXAMPLE 53

In vitro Activity of PA 824 Against *M. tuberculosis* in Human Macrophages

*M. tuberculosis* is very adept at survival within macrophage cells. To exert an effect, therefore, an antibiotic must be capable of penetrating the mammalian cell membrane, and, then remain stable within the hostile cellular environment. In addition, concentrations of the antibiotic at the intracellular site in which the pathogen resides must reach high enough levels to exert an effect. The pathogen burden within macrophages during the course of illness represents a sizable source of viable organisms, so that the ability to ascertain whether an antibiotic can affect these organisms is a useful criterion to predict therapeutic efficacy. In these studies, a bioluminescence assay was used to assess bacterial viability. *M. tuberculosis* $H_{37}Rv$ transformed with an integrative vector carrying the firefly luciferase gene as used as the challenge strain.

Human THP-1 monocytic cells (ATCC TIB-202) were differentiated into macrophages by treatment with 50 ng/ml phorbol 12-myristate 13-acetate (Sigma Chemical Co., St. Louis, Mo.) and were distributed at a density of $4\times10^5$ cells per ml to wells of a 48-well flat-bottom microtiter plate. After incubation at 37° C. for 48 h in a 5% $CO_2$ atmosphere, cell monolayers were washed with RPMI 1640 medium (GIBCO BRL, Grand Island, N.Y.) containing 10% heat-inactivated fetal bovine serum (FBS; HyClone Laboratories, Logan, Utah) and were infected with a logarithmic phase bacterial culture at a 1:1 multiplicity of infection. After incubation for 4 h at 37° C. in a 5% $CO_2$ atmosphere, the cells were washed five times with Hanks balanced salt solution (GIBCO BRL) to remove bacteria in the extracellular milieu. Eukaryotic cells were lysed by addition of 0.2 ml of phosphate buffered saline containing 1% Triton X-100. Aliquots of 0.1 ml of the lysate were transferred to an opaque white microtiter plate (MicroLite #1, Dynatech Inc., Chantilly, Va.) and luminescence determinations made in a Wallac Microlumat LB96P luminometer (Wallac Instruments, Gaithersburg, Md.) to obtain a day zero pretreatment reading. Alternatively, 0.2 ml aliquots were transferred to a Falcon 2054 test tube and RLU measurements made in a Wallac Autolumat LB 953 instrument. The luminometer automatically injected 0.1 ml of 1 mM luciferin (R & D Systems, Minneapolis, Minn.) prepared in 0.1 M trisodium citrate (pH5.1) into each tube or well. Luminescence was measured for 15 sec and expressed as relative light units (RLUs). Fresh medium (RPMI+10% FBS) was added to the remaining wells. To investigate the effects of antimycobacterial drugs, the medium was supplemented with selected concentrations of isoniazid or rifampin (Sigma) prepared in sterile deionized water or dimethyl sulfoxide (Sigma) respectively. Drug was either left in contact with the cells throughout the course of the experiment or was removed after 1.5 h by washing the monolayer with fresh RPMI medium. Cells in duplicate wells were lysed at desired daily intervals and the bioluminescence assay described above was performed. Both isoniazid and PA 824 were tested at concentrations equivalent to their in vitro MIC values, and at concentrations above and below this value. Controls were included which received no drug treatment, but were treated with sterile deionized water or DMSO to simulate the effects of the diluents used to prepare isoniazid and PA 824 respectively.

The macrophages themselves did not contribute to the luminescence reaction, since RLU levels for uninfected cells remained at background values throughout the course of the experiment. During this time, RLU values for macrophages infected with the recombinant *M. tuberculosis* strain increased dramatically reflecting intracellular growth of the recombinant bacteria. As shown in Tables 6–8, PA 824 concentrations of 0.25 μg/ml and greater were sufficient to prevent intracellular growth of *M. tuberculosis.* A clear dose-related response was observed at concentrations up to 2.0 μg/ml. Isoniazid achieved similar inhibition at concentrations above 0.06 μg/ml.

TABLE 6

RLU Values for Controls

| DAY | Cell Control | SD | Growth Control | SD | Growth Control + DMSO | SD |
|---|---|---|---|---|---|---|
| 0 | 151 | 25 | 20200 | 1110 | 13964 | 803 |
| 1 | 86 | 12 | 19692 | 1890 | 28702 | 1354 |
| 2 | 95 | 27 | 52181 | 1403 | 50024 | 2416 |
| 4 | 103 | 14 | 114513 | 15455 | 101129 | 3136 |
| 7 | 156 | 59 | 259773 | 203916 | 227767 | 70705 |

TABLE 7

RLU Values for INH Measured at 0.13, 0.06, and 0.03 μg/mL

| DAY | 0.13 | SD | 0.06 | SD | 0.03 | SD |
|---|---|---|---|---|---|---|
| 1 | 31113 | 6631 | 32192 | 1854 | 20360 | 4521 |
| 2 | 33898 | 5030 | 36680 | 1583 | 61355 | 32588 |
| 3 | 36634 | 2116 | 40344 | 5655 | 89528 | 1009 |
| 4 | 25282 | 2378 | 27408 | 8231 | 68253 | 1475 |
| 7 | 13373 | 2409 | 15855 | 1242 | 89032 | 15647 |

TABLE 8

RLU Values for PA 824 Measured at 2.0–0.6 μg/mL

| DAY | 2.0 | SD | 1.0 | SD | 0.5 | SD | 0.25 | SD | 0.13 | SD | 0.06 | SD |
|---|---|---|---|---|---|---|---|---|---|---|---|---|
| 1 | 4571 | 502 | 8197 | 769 | 10021 | 377 | 15814 | 579 | 16904 | 2032 | 25856 | 1122 |
| 2 | 3833 | 220 | 5588 | 482 | 9610 | 2199 | 18064 | 1253 | 40573 | 4116 | 93959 | 10793 |
| 3 | 2567 | 196 | 3950 | 823 | 6579 | 1182 | 13413 | 886 | 29162 | 3058 | 109301 | 10727 |
| 4 | 1507 | 71 | 2686 | 580 | 5068 | 817 | 8684 | 280 | 27802 | 612 | 118318 | 24962 |
| 7 | 1217 | 22 | 1986 | 102 | 2957 | 834 | 6437 | 867 | 28699 | 412 | 138792 | 21924 |

RLU values are means of four determinations
SD: standard deviation from the me

EXAMPLE 54

Inhibitory Concentration Values for 3(S) Substituted 6-Nitro-2H-3,4-dihydro-[2-1b] imidazopyran Compounds Against the Intestinal Protozoan *Cryptosporidium parvum*

Susceptibility testing against Cryptosporidium was performed according to published procedures (K. Woods, M. Nesterenko, S. Upton, "Development of a microtiter ELISA to quantify development of *Cryptosporidium parvum* in vitro," *FEMS Microbiology Letters,* 128:89–94 (1995).

Compounds were solubilized to a concentration of 100 mg/mL in 100% DMSO. DMSO solutions of test compounds were added to the test wells of a microplate at a volume that produced a final concentration of DMSO of 0.2%. Monolayers of human ileocecal adenocarcinoma cells (HCT-8) were prepared by growth in RPMI 1640 medium in 96-Well tissue culture trays for 24 h. Oocysts of *C. parvum* were allowed to excyst in 10% bleach for 10 min prior to use. Monolayers were then infected with 2–3x$10^4$ oocysts/well and incubated in the presence or absence of compound for 48 h at 35° C. in 5% $CO_2$ and 95% humidity. Background consisted of wells containing killed oocysts (freeze thaw cycle following 30 sec exposure to liquid nitrogen). Growth control wells were infected with 2–3x$10^4$ oocysts/well in the absence of test compounds. At the end of incubation, wells were washed and fixed by adding 100 uL of 4% formalin in phosphate buffered saline (pH 7.3) per well for 2 h. After blocking with 1% bovine serum albumin, and 0.002% Tween 20, 50 uL of rat anti-Cryptosporidium membrane protein antiserum was added. After 30 min, wells were washed in PBS and 50 uL of secondary antibody (goat anti-rat antibody conjugated with horseradish peroxidase) was added. After 20–30 min, wells were washed again in PBS and 50 uL of 3,3',5,5'-tetramethylbenzidine solution was added. Plates were allowed to develop for 10–15 min and the optical density was read at 630 nm. Percent inhibition was calculated by comparing the optical density of the drug treated group to that of the untreated control. As shown in Table 9, PA 824 at a concentration of 25 μg/mL inhibited growth by 52% (IC50=25 mg/mL). A clear dose-related response was also observed for PA 824.

The inhibitory concentrations of various 3(S) substituted 6-nitro-2H-3,4-dihydro-[2-1b]imidazopyran antibacterial compounds against *Cryptosporidium parvum* using the method described above were determined for compounds synthesized using the procedures described herein having the general structure:

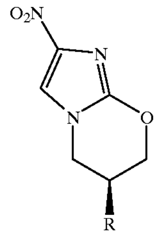

where R is the substituent shown in Table 1. Results are shown in Table 9.

TABLE 9

Percent Inhibition of *C. parvum* by the Indicated PA Compound

| Concentration (μg/mL) | PA No. 636 | 736 | 1122 | 1139 | 1150 | 1170 | 1298 | 824 |
|---|---|---|---|---|---|---|---|---|
| 5 | NT | NT | NT | NT | NT | NT | NT | 3.1 |
| 10 | NT | NT | NT | NT | NT | NT | NT | 17 |
| 20 | NT | NT | NT | NT | NT | NT | NT | 40 |
| 25 | 14.5 | −3.2 | −1.8 | −13 | 4.8 | −3 | 11.9 | 52 |
| 50 | 9.4 | 3 | 17.8 | −3 | 1.7 | −6 | 30 | 93 |
| 100 | 21 | 45 | 61 | 56 | 30 | 16 | 85 | 87 |
| 200 | 39 | 97.7 | 83.5 | 98.9 | 96.2 | −3.6 | Toxic | PPT |

NT = Not tested

EXAMPLE 55

In vivo Activity of 6-Nitro-2H-3,4-dihydro-[2-1b] imidazopyran Compounds Against *Helicobacter pylori* Strain 4187E Outbred female white mice (20 grams) were infected by oral gavage with $10^7$–$10^8$ colony forming units of *H. pylori* strain 4187E (originally isolated from a patient with a duodenal ulcer). After infection had become established, the mice were segregated to allow ten animals per group, and were treated twice daily by oral gavage with 50 mg/kg of test drugs prepared in the CM-2 formulation vehicle (Example 52). Treatment continued for four days. Clarithromycin, administered at the same concentration and for the same duration, was included as a positive control. One group of animals also received an equal volume of formulation vehicle alone, to provide a negative control.

Five days after cessation of treatment, all animals were sacrificed, the stomachs were removed, opened, and the contents washed out. The entire mucosal surface was then spread evenly over the surface of an agar plate containing antibiotics appropriate for the prevention of growth of microorganisms other than Helicobacter spp. After seven days incubation under microaeropilic conditions at 37° C., culture plates were evaluated for bacterial growth. The results are shown in the following Table 10:

TABLE 10

In vivo Activity of 6-Nitro-2H-3,4-dihydro-[2-1b]imidazopyran Compounds Against *Helicobacter pylori* Strain 4187E

| Compound | Dosing Regimen | Dose (mg/kg) | % Eradication |
|---|---|---|---|
| PA-822 | Once daily | 25 | 0 |
| | Twice Daily | 5 | 0 |
| | Twice Daily | 50 | 0 |
| PA-824 | Once daily | 25 | 0 |
| | Twice Daily | 5 | 10 |
| | Twice Daily | 50 | 100 |
| PA-1297 | Once daily | 25 | 0 |
| | Twice Daily | 5 | 0 |
| | Twice Daily | 50 | 0 |
| Clarithromycin | Twice Daily | 5 | 0 |
| | Twice Daily | 50 | 100 |
| CM-2 | Twice Daily | — | 10 |
| Milli-Q $H_2O$ | Twice Daily | — | 10 |

EXAMPLE 56

In vivo Activity of 6-Nitro-2H-3,4-dihydro-[2-1b] imidazopyran Compounds Against *Helicobacter felis*

Female CD-1 mice weighing 30 grams were infected by oral gavage with $10^8$–$10^9$ colony forming units of *H. felis*. This infection process was repeated two, and four days, thereafter. Colonization of the stomach was allowed to occur over a seven day period. Animals were segregated into groups of five, and were treated three times daily by oral gavage with 50 mg/kg of test drugs prepared in the CM-2 formulation vehicle (Example 52). Treatment continued for four days. One group of animals received an equal volume of formulation vehicle alone, to ensure that the vehicle had no effect on the Helicobacter infection. A separate untreated control group was also included.

All animals were then sacrificed, the stomachs were removed, opened, and the contents washed out. A five millimeter diameter biopsy was removed, and transferred to a urease test solution containing a pH-sensitive dye, which was then incubated at 37° C. incubator for 24 hours. A blue or purple coloration in this test solution signifies a positive reaction, indicating the continued presence of viable Helicobacter bacteria; a negative result is indicated by a yellow coloration. Viable Helicobacter bacteria produce a urease enzyme which converts urea, of which there is an abundant supply in the stomach (from saliva and gastric juices), into bicarbonate and ammonia, which are strong bases. This mechanism is considered to provide conditions more amenable to the survival of Helicobacter in the otherwise acidic conditions prevalent in the stomach. The results are shown in the following Table 11:

TABLE 11

In vivo Activity of 6-Nitro-2H-3,4-dihydro-[2-1b]imidazopyran Compounds Against *Helicobacter felis*

| Compound | % Survival |
|---|---|
| vehicle | 100 |
| untreated | 100 |
| PA-647 | 100 |
| PA-822 | 100 |
| PA-824 | 40 |
| PA-1297 | 100 |
| PA-1343 | 00 |

Various modifications and applications of the methods of the invention will be apparent from the foregoing to those skilled in the art. Any such modifications and applications are intended to be within the scope of the appended claims except insofar as precluded by the prior art.

What is claimed is:

1. An antibacterial compound selected from the group consisting of 3S n-octyloxy-6-nitro-2H-3,4-dihydro-[2-1b] imidazopyran; 3R n-octyloxy-6-nitro-2H-3,4-dihydro-[2-1b]imidazopyran; 4-benzyloxybenzyl carbamate of 3R-hydroxy-6-nitro-2H-3,4-dihydro-[2-1b]imidazopyran; 4-benzyloxybenzylamine amide of 3R-carboxylate-6-nitro-2H-3,4-dihydro-[2-1b]imidazopyran; 4-benzyloxybenzamide of 3R-amino-6-nitro-2H-3,4-dihydro-[2-1b]imidazopyran; N-methyl, N-4-benzyloxybenzyl 3R-amino-6-nitro-2H-3,4-dihydro-[2-1b] imidazopyran; 4-trifluoromethoxyphenylacetamide of 3S-(4-amino)-6-nitro-3,4-dihydro-[2-1b]imidazopyran; phenylacetamide of 3S-amino-6-nitro-3,4-dihydro-[2-1b] imidazopyran; 4-trifluoromethoxybenzyl carbamate of 3S 3-hydroxy-6-nitro-3,4-dihydro-[2-1b]imidazopyran; 4-bromophenyl carbamate of 3S hydroxy-6-nitro-2H-3,4-dihydo-[2-1b] imidazopyran; 4-(trifluoromethoxy)phenyl carbamate of 3S hydroxy-6-nitro-2H-3,4-dihydo-[2-1b] imidazopyran; 4-(trifluoromethyl)phenyl carbamate of 3S hydroxy-6-nitro-2H-3,4-dihydo-[2-1b] imidazopyran; 4-(trifluoromethoxy)benzyl carbamate of 3S hydroxy-6-nitro-2H-3,4-dihydo-[2-1b]imidazopyran; 3S 4-(trifluromethyl)benzyloxy-6-nitro-2H-3,4-dihydo-[2-1b] imidazopyran; 4-(2,2,2-trifluoroethoxy)phenyl carbamate of 3S hydroxy-6-nitro-2H-3,4-dihydo-[2-1b] imidazopyran; 4-(2,2,3,3-tetrafluoropropoxy)phenyl carbamate of 3S hydroxy-6-nitro-2H-3,4-dihydo-[2-1b] imidazopyran; 4-(2,2,3,3,3-pentafluoropropoxy)phenyl carbamate of 3S hydroxy-6-nitro-2H-3,4-dihydo-[2-1b] imidazopyran; 3S 4-(trifluromethoxy)benzyloxy-6-nitro-2H-3,4-dihydro-[2-1b] imidazopyran; 3S 4-(iodo)benzyloxy-6-nitro-2H-3,4-dihydo-[2-1b] imidazopyran; 3S 4-(trifluoroethoxy) benzyloxy-6-nitro-2H-3,4-dihydo-[2-1b] imidazopyran; 3S 4-(2,2,3,3-tetrafluoropropoxy)benzyloxy-6-nitro-2H-3,4-dihydo-[2-1b] imidazopyran; 3S 4-(2,2,3,3,3-pentafluoropropoxy)benzyloxy-6-nitro-2H-3,4-dihydo-[2-1b] imidazopyran; 4-chlorobenzyl carbamate of 3S 3-amino-6-nitro-3,4-dihydro-[2-1b]imidazopyran; 4-bromobenzyl carbamate of 3S 3-hydroxy-6-nitro-3,4-dihydro-[2-1b]imidazopyran; 4-chlorophenyl urea of 3S 3-amino-6-nitro-3,4-dihydro-[2-1b]imidazopyran; 2-(5-chlorobenzimidazole) derivative of 3S 3-Amino-6-nitro-3,4-dihydro-[2-1b]imidazopyran; and the stereoisomers and pharmaceutically acceptable salts thereof.

2. A method of inhibiting the growth of pathogenic microbes, comprising contacting the microbes with a growth inhibitory amount of a compound of claim 1.

3. The method of claim 2 wherein the pathogenic microbes are selected from the group consisting of *Mycobacteria tuberculosis, Mycobacteria leprae*, and *Mycobacteria avium* complex.

4. The method of claim 3 wherein the pathogenic mycobacterium is *Mycobacteria tuberculosis.*

5. The method of claim 3 wherein the pathogenic mycobacterium is a multidrug-resistant strain of *Mycobacteria tuberculosis.*

6. A method of treating a human or animal subject suffering from an infection by pathogenic microbes, comprising administering to the subject a therapeutically effective amount of a compound selected from the group consisting of 4-trifluoromethoxybenzyl carbamate of 3S 3-hydroxy-6-nitro-3,4-dihydro-[2,1b]imidazopyran, 4-(trifluoromethyl)phenyl carbamate of 3S hydroxy-6-nitro-2H-3,4-dihydro-[2,1b]imidazopyran, 3S 4-(trifluoromethyl) benzyloxy-6-nitro-2H-3,4-dihydro-[2,1b]imidazopyran, 3S 4-(trifluoromethoxy)benzyloxy-6-nitro-2H-3,4-dihydro-[2,1b]imidazopyran, 4-bromobenzyl carbamate of 3S 3-hydroxy-6-nitro-3,4-dihydro-[2,1b]imidazopyran, 4-chlorophenyl urea of 3S 3-amino-6-nitro-3,4-dihydro-[2,1b]imidazopyran, and the stereoisomers and pharmaceutically acceptable salts thereof.

7. A compound of claim 1 selected from the group consisting of 4-trifluoromethoxybenzyl carbamate of 3S 3-hydroxy-6-nitro-3,4-dihydro-[2,1b]imidazopyran, 4-(trifluoromethyl)phenyl carbamate of 3S hydroxy-6-nitro-2H-3,4-dihydro-[2,1b]imidazopyran, 3S 4-(trifluoromethyl) benzyloxy-6-nitro-2H-3,4-dihydro-[2,1b]imidazo-pyran, 3S 4-(trifluoromethoxy)benzyloxy-6-nitro-2H-3,4-dihydro-[2,1b]imidazopyran, 4-bromobenzyl carbamate of 3S 3-hydroxy-6-nitro-3,4-dihydro-[2,1b]imidazopyran, 4-chlorophenyl urea of 3S 3-amino-6-nitro-3,4-dihydro-[2,1b]imidazopyran, and the stereoisomers and pharmaceutically acceptable salts thereof.

* * * * *